US005284874A

United States Patent [19]

Clark et al.

[11] Patent Number: 5,284,874
[45] Date of Patent: * Feb. 8, 1994

[54] CHEMICAL PREVENTION OR REVERSAL OF CATARACT BY PHASE SEPARATION INHIBITORS

[75] Inventors: John I. Clark, Seattle, Wash.; George B. Benedek, Belmont, Mass.

[73] Assignee: Massachusetts Institute of Technology, Cambridge, Mass.

[*] Notice: The portion of the term of this patent subsequent to Feb. 25, 2009 has been disclaimed.

[21] Appl. No.: 942,326

[22] Filed: Sep. 9, 1992

Related U.S. Application Data

[63] Continuation of Ser. No. 451,955, Dec. 15, 1989, abandoned, which is a continuation-in-part of Ser. No. 198,850, May 26, 1988, abandoned, which is a continuation-in-part of Ser. No. 58,140, Jun. 4, 1987, abandoned.

[51] Int. Cl.$^5$ ............................................. A61K 31/16
[52] U.S. Cl. ..................................... 514/616; 514/912
[58] Field of Search ............... 514/114, 425, 563, 616, 514/912

[56] References Cited

U.S. PATENT DOCUMENTS

| 2,411,572 | 11/1946 | Dickey et al. | 260/461 |
|---|---|---|---|
| 3,124,508 | 3/1964 | Nordmann | 167/65 |
| 3,892,824 | 7/1975 | Piper et al. | 260/944 |
| 3,920,810 | 11/1975 | Rankin | 424/80 |
| 4,080,264 | 3/1978 | Cohen et al. | 195/103.5 A |
| 4,350,163 | 9/1982 | Ford, Jr. et al. | 128/633 |
| 4,350,677 | 9/1982 | von Schulthess et al. | 424/12 |
| 4,351,826 | 9/1982 | Clark et al. | 424/81 |
| 4,424,216 | 1/1984 | Cerami et al. | 424/211 |
| 4,451,477 | 5/1984 | Silvestrini et al. | 424/273 |
| 4,474,817 | 10/1984 | Clark et al. | 424/333 |
| 4,526,789 | 7/1985 | Clark et al. | 514/627 |
| 4,537,892 | 8/1985 | York et al. | 514/278 |
| 4,611,074 | 9/1986 | Shealy et al. | 558/51 |
| 4,656,034 | 4/1987 | Sarnoff | 424/94 |
| 4,665,089 | 5/1987 | Siezen et al. | 514/422 |
| 4,702,576 | 10/1987 | Magnante | 351/214 |
| 4,711,542 | 12/1987 | Ichihashi et al. | 351/221 |
| 4,719,912 | 1/1988 | Weinberg | 128/303.1 |
| 4,727,174 | 2/1988 | Shealy et al. | 558/51 |

FOREIGN PATENT DOCUMENTS

| 199103A2 | 10/1986 | European Pat. Off. | A61K 31/22 |
|---|---|---|---|
| 60-139618 | 7/1985 | Japan | A61K 31/16 |

OTHER PUBLICATIONS

Lubin et al., "Dimethyl Adipimidate: A New Antisickling Agent," *Proc. Natl. Acad. Sci. USA* 72(1):43–6, 1975.
Waterman et al., "Anti-Sickling Nature of Dimethyl Adipimidate," *Biochem. Biophys. Res. Com.* 63(3):580–7, 1975.
Jedziniak et al., "The Concentration and Localization of Heavy Molecular Weight Aggregates in Aging Normal and Cataractous Human Lenses," *Exp. Eye Res.* 20:367–69, 1975.
Biosis 83080591 (1986) Osgood et al.
Efimov et al., "The Role of Sorbitol Metabolic Pathway in Therapeutic Mechanisms of Pantethine in Diabetic Models," *Khim-FarmZH* 20(8):912–4, 1986 (English translation enclosed).
Tsutsumi et al., "Wirkung von Pantothensäurenderivaten auf den durch Hyperlaktosediät hervorgerufenen Katarakt in Ratten," *Deutsche Aoptheker-Zeitung* 108(33)1204, 1968 (English translation enclosed).
Zigman and Lerman, "A Cold Precipitable Protein in the Lens," *Nature* 203:662–3, 1964.
Dubin et al., "Observation of the Spectrum of Light Scattered by Solutions of Biological Macromolecules," *Proc. Natl. Acad. Sci. USA* 57(5):1164–71, 1967.
N. Clark et al., "A Study of Brownian Motion Using Light Scattering," *Am. Jour. Phys.* 38(5):575–85, 1970.

(List continued on next page.)

*Primary Examiner*—Zohreh A. Fay
*Attorney, Agent, or Firm*—Seed and Berry

[57] ABSTRACT

The present invention relates to methods and pharmaceutical reagents for decreasing the phase separation temperature and inhibiting the formation of high molecular weight aggregates in eye lenses, thereby inhibiting or reversing cataract formation.

1 Claim, 23 Drawing Sheets

OTHER PUBLICATIONS

Benedek, "Theory of Transparency of the Eye," *Applied Optics* 10:459-73, 1971.

Jedziniak et al., "Calcium-Induced Aggregation of Bovine Lens Alpha Crystallins," *Invest. Ophthal.* 2:905-15, 1972.

Jedziniak et al., "On the Presence and Mechanism of Formation of Heavy Molecular Weight Aggregates in Human Normal and Cataractous Lenses," *Exp. Eye Res.* 15:185-92, 1973.

Tanaka and Benedek, "Observation of Protein Diffusivity in Intact Human and Bovine Lenses with Application to Cataract," *Invest. Ophthal.* 14(6):449-56, 1975.

Jedziniak et al., "On the Calcium Concentration of Cataractous and Normal Human Lenses and Protein Fractions of Cataractous Lenses," *Exp. Eye Res.* 23:325-32, 1976.

Tanaka and Ishimoto, "*In Vivo* Observation of Protein Diffusivity in Rabbit Lenses," *Invest. Ophthal.* 16(2):135-40, 1977.

Lion Dentifrice Co., Ltd., "Stable Eye Drops Containing Pantothenic Acid," Japan Kokai 78 62,820, Jun. 5, 1978 (cited in *Chem. Abstracts* 89:1358773, 1978).

Jedziniak et al., "Quantitative Verification of the Existence of High Molecular Weight Protein Aggregates in the Intact Normal Human Lens by Light-Scattering Spectroscopy," *Invest. Ophthal. Vis. Sci.* 17(1):51-7, 1978.

Benedek et al., "Light Scattering and Reversible Cataracts in the Calf and Human Lenses," *Phil. Trans. R. Soc. Lond.* A293:329-40, 1979.

Ishimoto et al., "Cytoplasmic Phase Separation in Formation of Galactosemic Cataract in Lenses of Young Rats," *Proc. Natl. Acad. Sci. USA* 76(9):4414-36, 1979.

Clark and Benedek, "The Effects of Glycols, Aldehydes and Acrylamide on Phase Separation and the Opacification in the Calf Lens," *Invest. Ophthal. Vis. Sci.* 19(7):771-6, 1980.

Clark and Benedek, "Phase Diagram for Cell Cytoplasm From the Calf Lens," *Biochem. Biophys. Res. Com.* 95(1):482-9, 1980.

Siezen et al., "The Quaternary Structure of Bovine α-Crystallin," *Eur. J. Biochem.* 107:243-9, 1980.

Clark et al., "Cortical Opacity, Calcium Concentration and Fiber Membrane Structure in the Calf Lens," *Exp. Eye Res.* 31:399-410, 1980.

Benedek and Clark, "Light Scattering in the Lens: Phase Transition and Opacification," *Developments in Biochem 9, Red Blood Cell and Lens Metabolism* (Srivastava ed.), pp. 431-4, 1980.

Clark et al., "Scanning Electron Microscopy of Opaque and Transparent States in Reversible Calf Lens Cataracts," *Ophthal. Res.* 12:16-33, 1980.

Clark et al., "Laser Light Scattering and Cataract," *Proc. of Tech. Conf. on Electro-Optics and Lasers*, pp. 365-70, 1981.

Delaye et al., "Coexistence Curves for Phase Separation in the Calf Lens Cytoplasm," *Biochem. Biophys. Res. Com.* 100:908-14, 1981.

Clark et al., "Phase Separation in X-Irradiated Lenses of Rabbit," *Invest. Ophthal. Vis. Sci.* 22(2):186-90, 1982.

Delaye et al., "Identification of the Scattering Elements Responsible for Lens Opacification in Cold Cataracts," *Biophys J.* 37:647-56, 1982.

Nemes et al., "Chemical Modification of Rhodopsin With Imidoesters: Synthesis of Reagents, Membrane Permeability of Reagents, and Modification Methods," *Methods in Enzymol.* 81:275-85, 1982.

Clark et al., "Preparation and Characterization of Native Lens Cell Cytoplasm," *Curr. Eye Res.* 1:695-704, 1982.

Ross et al., "Radiation Cataract Formation Diminished by Vitamin E in Rat Lenses *In Vitro*," *Exp. Eye Res.* 36(5):645-53, 1983.

Tanaka et al., "Phase Separation in Rat Lenses Cultured in Low Glucose Media," *Invest. Ophthal. Vis. Sci.* 24(4):522-5, 1983.

Middaugh et al., "Chemical Crosslinking of Cell Membranes," *Molecular and Cellular Biochem.* 50:115-41, 1983.

Benedek, "Why the Eye Lens is Transparent," *Nature* 302(5907):383-384, 1983.

Davidson et al., "Biological Characteristics of Some Improved Radioprotectors," *Radiation Sensitizers*, pp. 308-320, 1983.

Kador, "Overview of the Current Attempts Toward the Medical Treatment of Cataract," *Ophthalmology* 90(4):352-64, 1983.

Clark et al., "Phase Separation and Lens Cell Age," *J. Gerontol.* 38:287-92, 1983.

Hammer and Benedek, "The Effect of Naturally Occurring Cellular Constituents on Phase Separation and Opacification in Calf Lens Nuclear Homogenates," *Curr. Eye Res.* 2(12):809-14, 1983.

OTHER PUBLICATIONS

Zeimer and Noth, "A New Method of Measuring *In Vivo* the Lens Transmittance, and Study of Lens Scatter, Fluorescence and Transmittance," *Ophthal. Res.* 16(5):246-55, 1984.

Nishio et al., "*In Vivo* Observation of Lens Protein Diffusivity in Normal and X-Irradiated Rabbit Lenses," *Exp. Eye Res.* 39(1):61-8, 1984.

"Chemical Protection Against Ionizing Radiation," Federal Emergency Management Agency, Final Report, 1984.

Benedek, "The Molecular Basis of Cataract Formation" *Human Cataract Formation* CIBA Foundation Symposium 106, pp. 236-47, 1984.

Creighton et al., "Modeling Cortical Cataractogenesis VII: Effects of Vitamin E Treatment on Galactose-Induced Cataracts," *Exp. Eye. Res.* 40(2):213-22, 1985.

Libondi et al., "*In Vitro* Effect of Alpha-Tocopherol on Lysophosphatidylcholine-Induced Lens Damage," *Exp. Eye. Res.* 40(5):661-6, 1985.

Crompton et al., "Aspirin Prevents Carbamylation of Soluble Lens Proteins and Prevents Cyanate-Induced Phase Separation Opacities *In Vitro:* A Possible Mechanism by Which Aspiring Could Prevent Cataract," *Exp. Eye Res.* 40(2):297-311, 1985.

Siezen et al., "Permanent Suppression of Phase Separation Cataract in Calf Lenses Using Amine Modification Agents," *Biochem. Biophys. Res. Com.* 133(1):239-47, 1985.

Siezen and Benedek, "Controlled Modulation of the Phase Separation and Opacification Temperature of Purified Bovine $_7$IV-Crystallin," *Current Eye Res.* 4(10):1077-85, 1985.

Weale, "Human Lenticular Fluorescence and Transmissivity, and Their Effects on Vision," *Exp. Eye Res.* 41(4):457-73, 1985.

Clark, "Bedeutung der Phase-Umwandlung fur die Katarktentwicklung?" *Biochemie des Auges,* D. Hockwin (ed.), pp. 290-99, 1985.

Neuringer et al., "Quantitative Microprobe Analysis of Elements in Cortical and Nuclear Cells of Calf Lens," *Anat. Rec.* 211:329-37, 1985.

Clark and Danford, "Low Temperature and Acrylamide Inhibit Lens Opacification Caused by Calcium," *Ophthal. Res.* 17:246-50, 1985.

Siezen et al., "Opacification of c-Crystallin Solutions From Calf Lens in Relation to Cold Cataract Formation," *Proc. Natl. Acad. Sci USA* 82:1701-5, 1985.

Libondi et al., "Osservazione *In Vivo* Mediante Quasi–Elastic Light Scattering Della Diffusivita' Di Proteine Del Cristallino Umano Normale," *Proc. of LXV Congresso Della Societa Oftalmologica Italiana,* pp. 319-24, 1985.

Menard et al., "Radioprotection Against Cataract Formation by WR-77913 in Gamma-Irradiated Rats," *Init. J. Radiation Oncology Biol. Phys.* 12(8):1483-6, 1986.

Osgood et al., "Inhibition of Lens Opacification in X-Irradiated Rats Treated with WR-77913," *Invest. Ophthal. Vis. Sci.* 27(12):1780-4, 1986.

DeSantis, "New Horizons in the Medical Therapy of Cataract: Aldose Reductase Inhibitors and Other Agents," *Pharm Intl.* 7(1):17-20, 1986.

Rosival et al., "Ochrana Cocky Pred Poskozenim Ionizujicim Zarenim Pomoci Gamafosu," *Cesk. Oftalmol.* 42(6):413-16, 1986 (English translation enclosed).

Osgood et al., "Inhibition of Opacification of X-Irradiated Rat Lenses," *Invest. Ophthal. Vis Sci.* 27(3), Supp. (1986). (Annual Spring Meeting of the Association for Research in Vision and Ophthalmology Inc., Sarasota, Florida, Apr. 28-May 2, 1986, Abstract No. 60).

Libondi et al., "*In Vivo* Measurement of the Aging Rabbit Lens Using Quasielastic Light Scattering," *Current Eye Res.* 5(6):411-19, 1986.

Magnante et al., "*In Vivo* Measurements on Human Lens Using Quasielastic Light Scattering," *Opt. and Laser Tech. in Med.* 605-94-97, 1986.

Clark and Carper, "Phase Separation in Lens Cytoplasms is Genetically Linked to Cataract Formation in the Philly Mouse," *Proc. Natl. Acad. Sci. USA* 84:122-5, 1987.

Clark et al., "Inhibition of Phase Separation by Reagents That Prevent X-Irradiation Cataract *In Vivo,*" *Exp. Eye Res.* 45(6):961-7, 1987.

Benedek et al., "Quantitative Detection of the Molecular Changes Associated with Early Cataractogenesis in the Living Human Lens Using Quasielastic Light Scattering," *Current Eye Res.* 6 (12):1421-32, 1987.

Shearer et al., "Selenite Cataract: A Review," *Current Eye Res.* 6 (2):289-300, 1987.

OTHER PUBLICATIONS

Eccarius and Clark, "Effect of Aspirin and Vitamin E on Phase Separation in Calf Lens Homogenate," *Ophthal. Res.* 19:65-71, 1987.

Siezen et al., "Human Lens λ-Crystallins: Isolation, Identification, and Characterization of the Expressed Gene Products," *Proc. Natl. Acad. Sci. USA* 84:6088-92, 1987.

Thomson et al., "Binary Liquid Phase Separation and Critical Phenomena in a Protein/Water Solution," *Proc. Natl. Acad. Sci. USA* 84:7079-83, 1987.

Dillon et al., "*In Vitro* and *In Vivo* Protection Against Phototoxic Side Effects of Photodynamic Therapy by Radioprotective Agents WR-2721 and WR-77913," *Photochem. Photobiol.* 48(2):235-8, 1988.

Sieven et al., "Rat Lens λ-Crystallins Characterization of the Six Gene Products and Their Spatial and Temporal Distribution Resulting From Differential Synthesis," *J. Mol. Biol.* 199:475-90, 1988.

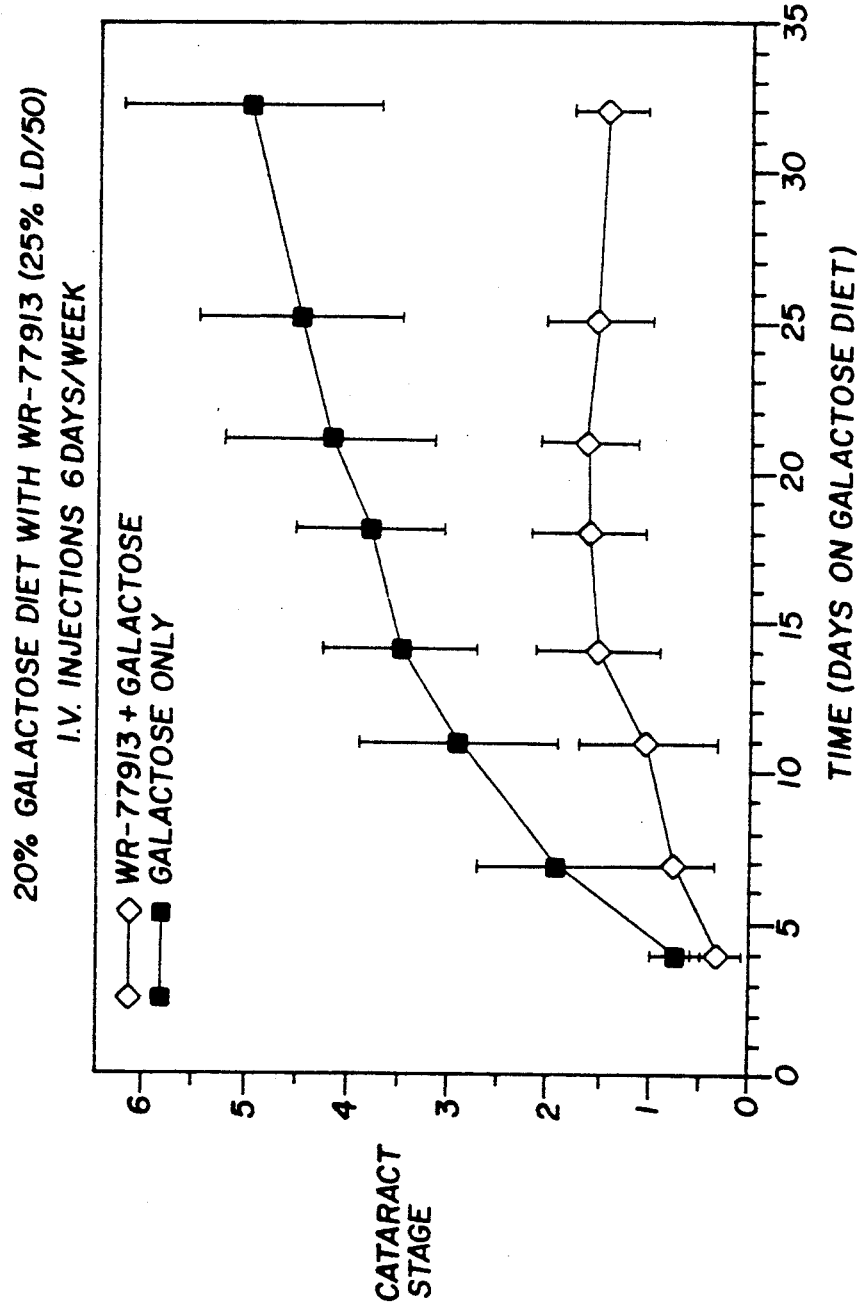

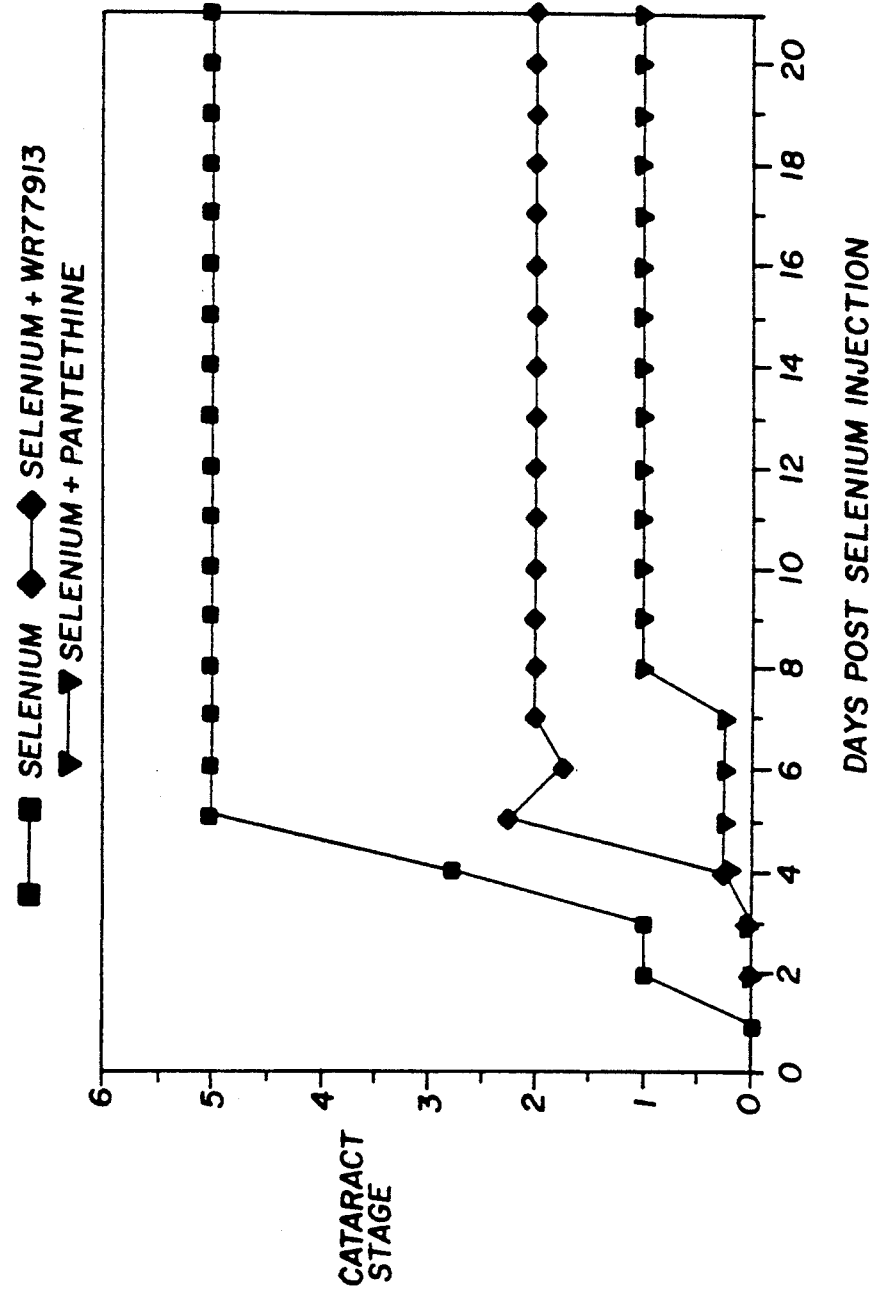

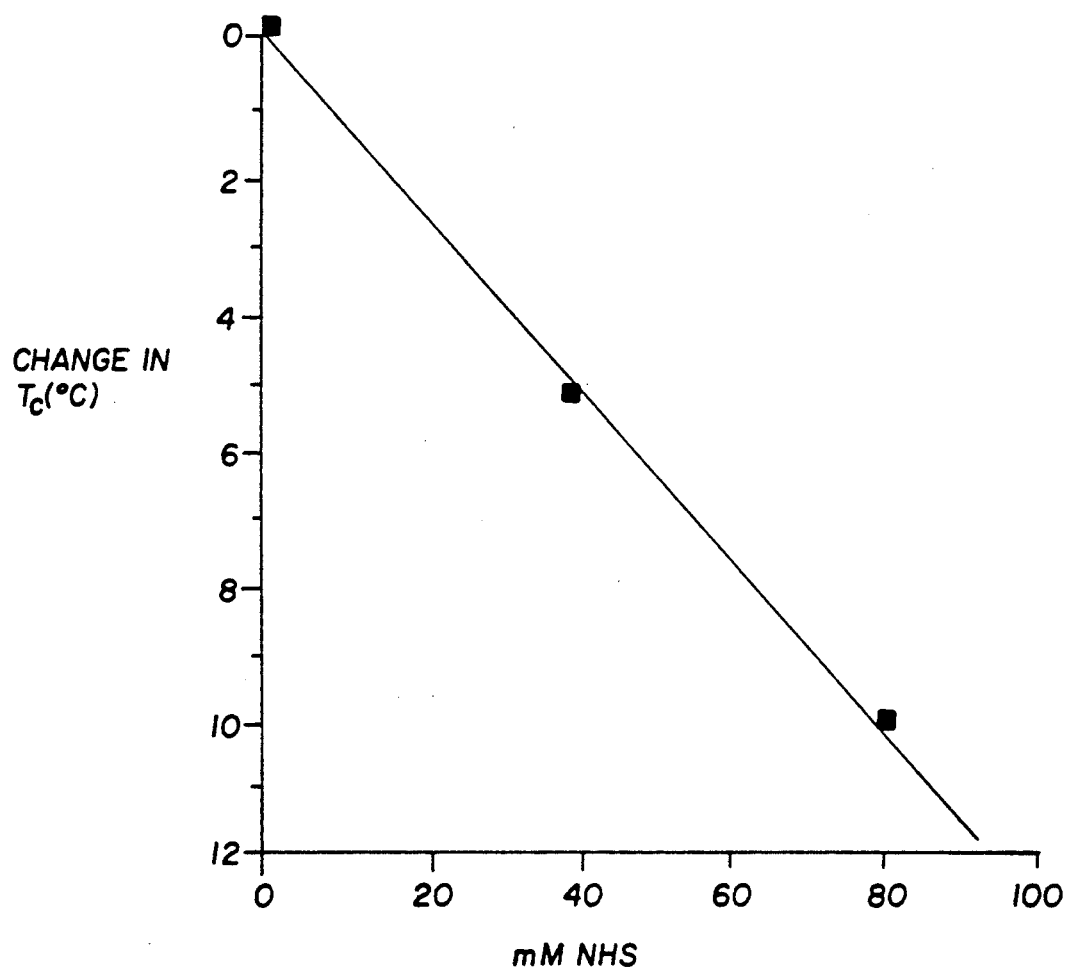

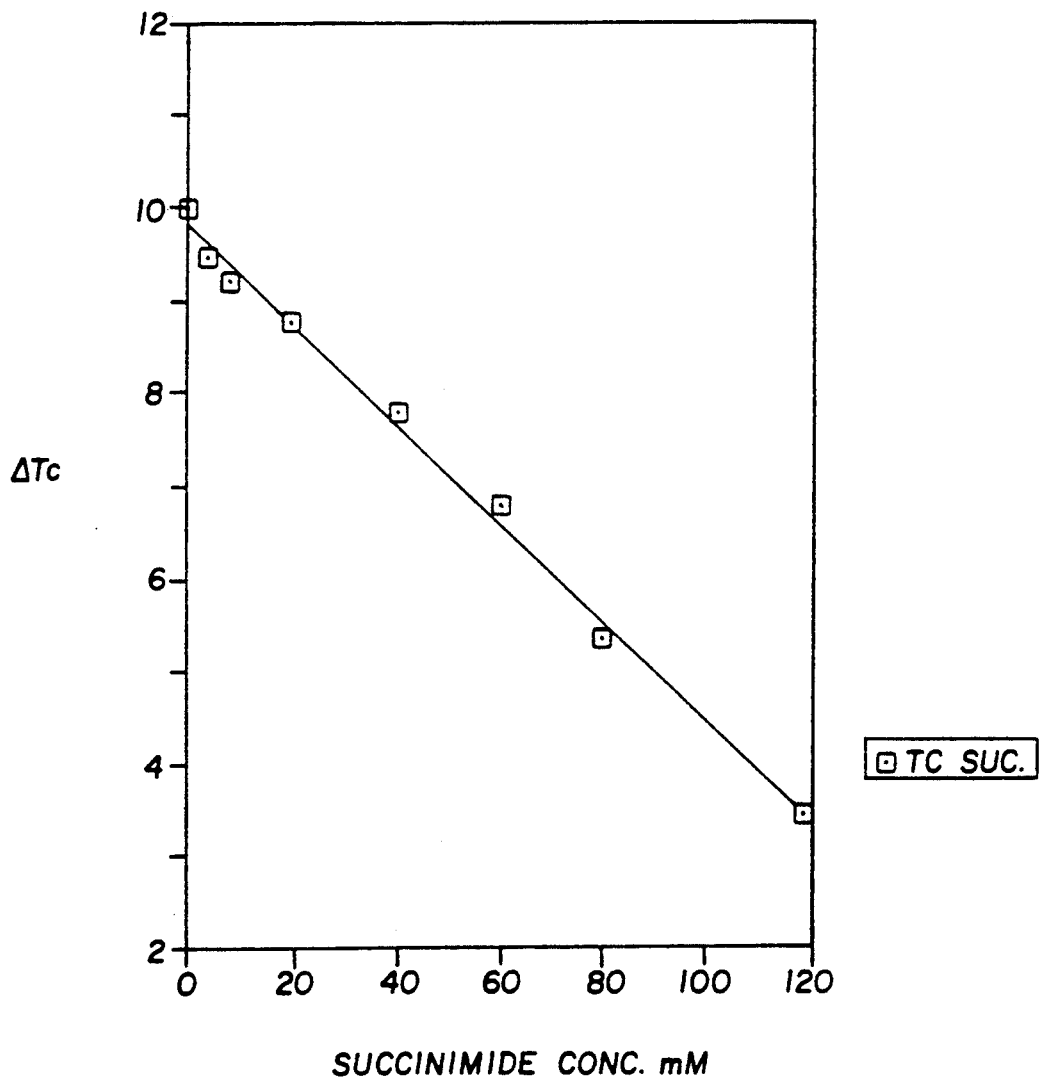

CHEMICAL PREVENTION OR REVERSAL OF CATARACT BY PHASE SEPARATION INHIBITORS

GOVERNMENT SUPPORT

The United States Government may have certain rights in this invention pursuant to National Institute of Health Grant Nos. NIH-5-R01-EY05127 and NIH-5-R01-EY05496.

RELATED APPLICATIONS

This application is a continuation of U.S. Ser. No. 07/451,955 filed on Dec. 15, 1989 now abandoned, which is a continuation-in-part of U.S. Ser. No. 198,850, filed May 26, 1988 now abandoned, which is a continuation-in-part of U.S. Ser. No. 058,140, filed Jun. 4, 1987 now abandoned.

TECHNICAL FIELD

The present invention relates generally to the area of pharmaceuticals and, more specifically, to compositions and methods for the prevention of cataracts.

BACKGROUND OF THE INVENTION

"Cataract" is the general term for any pathological condition in which the normal transparency of the ocular lens is substantially diminished. More than one million cataract extractions are performed annually in the United States, and it is estimated that 5 to 10 million individuals become visually disabled each year due to cataracts.

Although often regarded as an inevitable accompaniment of advancing age, cataracts may develop at any time in life, even before birth. Risk factors for cataract formation include metabolic disorders (e.g., diabetes), exposure to toxic agents in the environment (e.g., ultraviolet radiation, ionizing radiation), drug side effects, and inherited traits. Clinical experience suggests that the natural course of different types of cataracts are distinct. However, objective, quantitative data is generally lacking.

Development of anti-cataract agents has been hampered, in part, by the lack of a good animal model of human cataract. Consequently, putative anti-cataract agents may be evaluated for efficacy in a variety of different models which, to the extent that they are understood at all, are thought to occur by different mechanisms. For example, radiation-induced cataract is generally believed to result from oxidative damage to the lens. Diabetic cataract is thought to be due to the accumulation of polyols (such as sorbitol) in the lens, resulting from increased activity of the enzyme aldose reductase. Selenite-induced cataract is thought to be due to activation of a class of $Ca^{2+}$-dependent proteases in the lens. The Royal College of Surgeons (RCS) hereditary cataract is thought to be due to the action of products released by the retina. Because cataract in the various animal models is thought to occur by different biochemical mechanisms, it is generally believed that no single anti-cataract agent can be effective in all models.

In contrast to the understanding of cataract pathogenesis, the cellular structure of the lens is fairly well characterized. The lens exhibits a high degree of regularity, consisting of fiber cells with hexagonal cross sections packed together to create a very regular parallel array of fiber cells which stretch from anterior to posterior pole. The lens fiber cells lose all intracellular organelles that could contribute to light scattering during the process of differentiation and the cytoplasmic protein concentration increases markedly.

Approximately 35% to 60% of the total mass of the lens consists of structural proteins, the remainder being water. More than 90% of the total lens protein consists of alpha, beta, and gamma crystallins, a group of structural proteins found at extremely high concentrations (in excess of 300 mg/ml) in the lens cell cytoplasm. The cytoplasmic concentration of the crystallins throughout the lens occurs along a continuous radial concentration gradient, in which the concentration is greatest in cells at the nucleus and decreases in peripheral cells of the lens cortex. The crystallin distribution determines the mean index of refraction and index gradient, which are in turn responsible for the special optical properties of the animal lens.

An important optical property is lens transparency. In the normal lens, incident light is scattered in all directions by the macromolecular constituents of the lens. If the individual wavelets of the scattered light interfere destructively with one another, the lens is transparent. Destructive interference takes place in the normal lens because of the existence of short range order in the relative positions of the crystallins. If the uniformity of the protein concentration is sufficiently perturbed, a substantial fraction of the incident light is scattered in directions away from the forward direction. The scattering results in a distortion of the wave front of the transmitted light, and in opacity of the lens tissue. The opacity is responsible for visual impairment in cataract diseases.

Cataracts are the leading cause of blindness in humans worldwide, and surgery remains the primary form of treatment. Cataracts in animals also pose a significant veterinary problem. To date, a compound for in vivo administration to humans or other animals has not been demonstrated to prevent cataracts of diverse origin. Further, in vivo reversal of the initiation of cataract formation has not been successfully demonstrated.

Therefore, there is a significant need for an effective nonsurgical method for treating or preventing cataractogenesis in humans and other animals. This method should utilize compounds which are relatively safe and which may be conveniently administered. The present invention fulfills these needs and provides other related advantages.

SUMMARY OF THE INVENTION

The present invention provides an in vivo method and pharmaceutical reagents for preventing abnormal increases in phase separation temperature and prevention of cataract formation. The pharmaceutical reagents are able to diffuse into the lens and exert a prophylactic or therapeutic anti-cataractic effect over a reasonable period of time. Desirable reagents do not change the eye color or viscoelastic properties of the lens in a manner detrimental to visual acuity. In a preferred form, the reagents are applied locally (i.e., topically) to minimize the effective dose and possible side effects, but may also be administered systemically (e.g., orally or by injection).

The specific effect of the reagents is believed to be an inhibition to changes in spatial fluctuations in the index of refraction by maintaining the short range order in the lens proteins. This is accompanied by an inhibition to an increase in the phase separation temperature and by a suppression of the formation of high molecular weight aggregates. Temperatures for which phase separation occurs can be determined from a coexistence curve distinguishing the homogeneous from the heterogeneous phases. At temperatures outside (above) the coexistence curve, the lens cytoplasm exists as a homogeneous, transparent phase. At temperatures within (below) the coexistence curve, the cytoplasm separates into regions which are rich and poor in the constituent proteins. These regions, which have different indices of refraction, scatter light strongly and produce opacification.

Pathologic cataracts are characterized by disruption of membrane structure, the formation of high molecular-weight aggregates, and functional deterioration. These changes occur well after the first changes in phase separation temperature occurs. The phase separation temperature serves as a useful indicator of the earliest stages of cataract formation. The presence of high molecular weight aggregates, which scatter light and cause opacification, can be determined from the measurement of the intensity autocorrelation function of laser light scattered from the lens, where the width of the scattered light spectrum or the reciprocal of the correlation time of the scattered light intensity fluctuation decreases with the concentration of high molecular weight aggregates.

Examples of reagents or phase separation inhibitors (PSI) according to the present invention which have been demonstrated to meet the desired criteria and are useful in methods of treating and preventing cataracts in the lens of a mammal include phosphorothioate compounds of the general formula $RNHR_1SPO_3H_2$, in which R is hydrogen, an alkoxy group containing 1 to 6 carbon atoms or the group $R_2NH(C_nH_{2n})$-, in which $R_2$ is hydrogen or an alkyl group containing 1 to 6 carbon atoms and n has a value of from 2 to 6, $R_1$ is an optionally substituted alkylene group having from 1 to 6 carbon atoms, and hydrates or alkali metal salts thereof. Particularly preferred phosphorothioates are S-3-(amino-2-hydroxypropyl) phosphorothioate (WR-77913) and S-2-(3-aminopropylamino) ethyl phosphorothioate (WR-2721). Other compounds include succinimides and derivatives thereof, where preferred compounds are selected from the group consisting of succinimide, N-hydroxysuccinimide (NHS), and ethosuximide. Another group of reagents useful as pharmaceutical compositions inhibiting or reversing cataractogenesis comprises pantethine, pantetheine, pantothenic acid, and panthenol. Still other compounds include cysteamine. The pharmaceutical compositions may be utilized in the treatment methods herein described in a variety of ways, including topical administration as well as systemic or parenteral administration.

The subjects which may be benefited by the treatment methods of the invention include a variety of mammals which are susceptible to cataract development, such as equine, canine, and feline species, as well as humans.

BRIEF DESCRIPTION OF THE DRAWINGS

FIG. 5 is a graph of the inhibition of cataract by WR-77913 in animals on a galactose diet.

FIG. 6 is a graph of the inhibition of cataract development by WR-77913 and by pantethine in animals with selenium-induced cataract.

FIG. 7 is a graph of the change in phase separation temperature, Tc(°C.), of a calf lens versus concentration of NHS (mM).

FIGS. 8(a) and 8(b) are graphs of the change in phase separation temperature, Tc(°C.), versus concentration of succinimide and ethosuximide, respectively, for concentrated lens homogenates.

DETAILED DESCRIPTION OF THE SPECIFIC EMBODIMENTS

Figure 1:
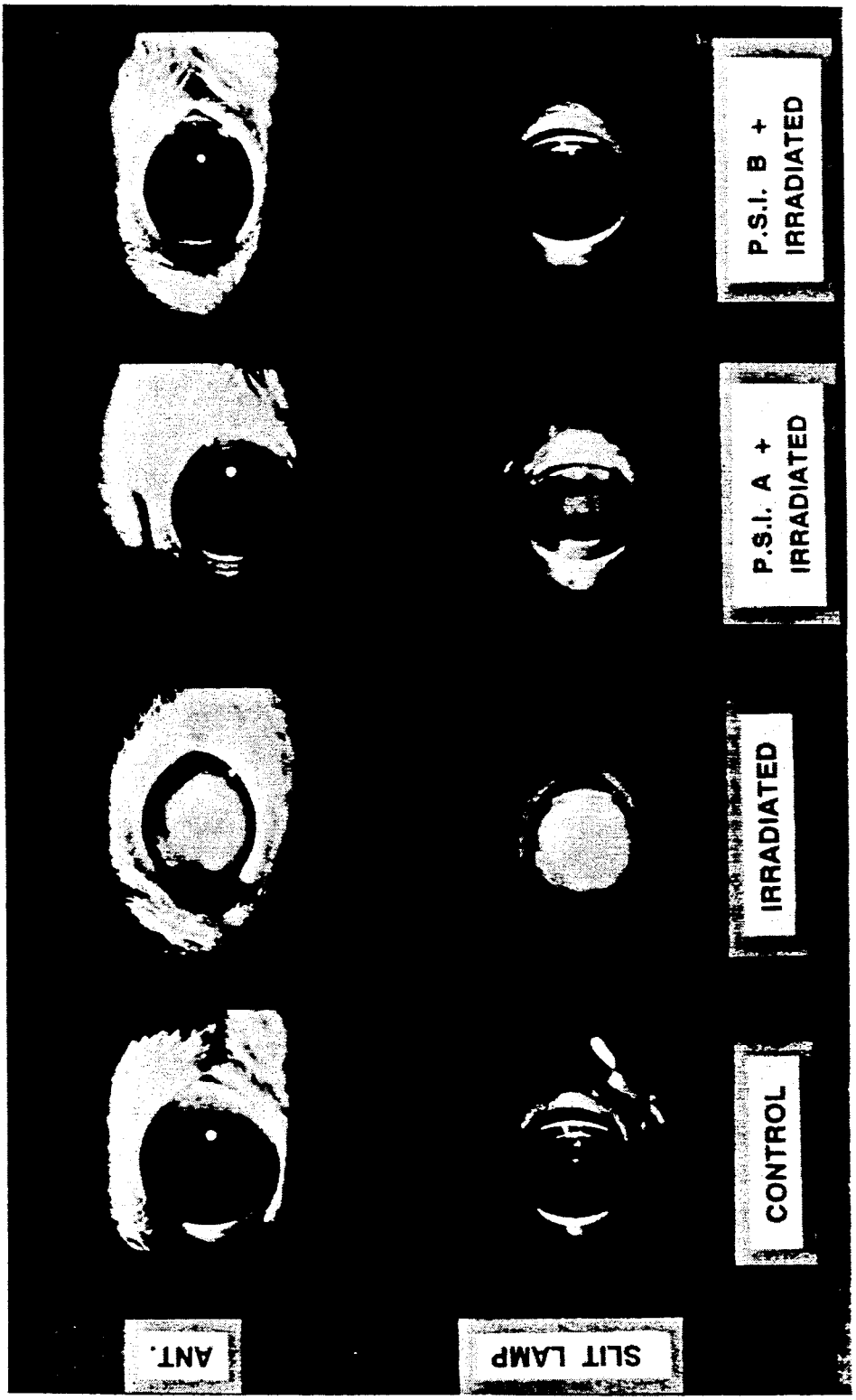
FIG. 1 is a photograph of control rat eyes compared to cataractous rat eyes, rat eyes treated with WR-77913 (PSI A), and rat eyes treated with pantethine (PSI B). The top row is a photograph of the eye of the animals and the row below is a slit-lamp photograph of the same eye. The first column is a normal eye of a control rat without any treatment. The second column is a cataract-induced eye approximately 150 days following irradiation. The last two columns show the eyes of animals that were administered PSI A or PSI B before administration of the cataractogenic insult.

The present invention is directed to compositions and methods which can inhibit or reverse cataract formation. The compositions and methods will effectively treat cataracts regardless of the source of the cataract. The invention pertains to pharmaceutical reagents and methods of treatment which lower the phase separation temperature of a lens and which prevent or inhibit the formation of opacities, high molecular weight aggregates, and other physical characteristics of cataracts.

The reagent compositions may be administered in a variety of ways, including topically or systemically, as further discussed below. Desirably, the reagents will be able to diffuse into the lens and will be relatively nontoxic to the lens and surrounding tissues, will have little or no adverse effect on the viscoelastic properties of the lens which affect visual acuity, and will desirably have no substantial effect on lens color.

The compounds may initially be screened in vitro for the ability to lower the phase separation temperature of a lens or a lens homogenate. The phase separation temperature of a lens is defined as the temperature at which, at a given protein concentration, the cytoplasm of the lens cells will separate into coexisting phases. The temperature is determined from a coexistence curve in a phase diagram plotting temperature (°C.) against protein concentration, where segregation occurs at a temperature and concentration under the curve.

For instance, a cytoplasmic phase separation is associated with the earliest stages of cataract formation produced by X-irradiation. The phase separation occurs over a narrow temperature range and is characterized by a phase separation temperature, Tc. In normal lenses, the Tc is well below body temperatures and the lenses are transparent. In X-irradiated lenses, Tc increases during the early stages of cataract formation. As the cataract progresses, membrane function is disrupted, ion levels change, high molecular weight aggregates are formed and an advanced cataract forms.

The Tc of a lens may be readily determined by means of laser transmittance, as described, for example, in Clark et al., *Invest. Ophthalmol.* 21:186, 1982, or in U.S. Pat. No. 4,665,089, which are incorporated by reference herein. A pair of lenses may be removed from a test animal, one eye of the animal having been X-irradiated and the other eye not. The lenses are placed in a cuvette filled with silicone oil, which is then mounted on a movable, temperature-controlled stage that is directly in the path of a laser beam, with the anterior surface facing the beam. The transmittance can be measured with this apparatus as a function of temperature at every region in the opaque lens. When the transmittance in the region of densest opacity reaches a predetermined percentage of its maximum value, such as 50%, 75%, or 90%, this temperature is defined as the Tc of the normal and irradiated lens during cataract development.

Other methods of determining the phase separation temperature include light scattering determinations. It should be noted that the value used for Tc will depend on the method used. For instance, with laser transmittance as described above, a value of 50%, 75%, or 90% may be used. Dynamic light scattering, a more sensitive method, may use 90% or 95% of the maximum value, such as described in Benedek et al., *Phil. Trans. R. Soc. Lond. A.* 293:329–340, 1979. The maximum value of light scattering was used in Ishimoto et al., *Proc. Natl. Acad. Sci. USA* 76:4414, 1979, to determine Tc, whereas Clark and Benedek, *Biochem. Biophys. Res. Comm.* 95:482–489, 1980, used 50% of the maximum value of transmittance. The latter article also describes a method for constructing phase diagrams for isolated lens cytoplasmic homogenate. Each of the foregoing articles is expressly incorporated herein by reference.

The reagents of the present invention also inhibit the formation of high molecular weight protein aggregates in the lens. By "inhibit" is meant to include the prevention or reversal of high molecular weight protein aggregate formation in the lens cytoplasm. The extent of protein aggregation in the lens may be determined in vitro by measuring the relative amount of insoluble protein, for example, as described in Osgood et al., *Invest. Ophthal. Vis. Sci.* 27:1780–1784, 1986, which is incorporated herein by reference. Alternatively, the formation of high molecular weight aggregates may be determined in the intact lens in situ by a number of well-known means, such as by fluctuations in scattered light intensity described in Tanaka and Benedek, *Invest. Ophthal.* 14:449–456, 1975; Delaye et al., *Biophys. J.* 37:647–656, 1982; U.S. Pat. No. 4,702,576; or as described in copending patent applications U.S. Ser. Nos. 091,658 and 091,834, all of which are incorporated herein by reference.

To monitor the effect of a compound or reagent on the formation of high molecular weight aggregates, the composition may be administered to an animal by any of several different routes and in a variety of formulations and concentrations, depending on the characteristics of the composition being tested. For instance, a composition may be administered topically or systemically, prior to or following the induction of the cataractic process, such as X-irradiation. The high molecular weight aggregates in the lenses of treated animals may be monitored for a period of time and compared to appropriate untreated controls. Reagent compositions of the invention will desirably inhibit the formation of such aggregates and prevent or delay the further development of cataracts in the treated animals. The lenses of the treated animals may also be removed and the Tc determined as explained above.

There are several established animal models for cataracts in which the reagents of the present invention may be screened and evaluated. These include (1) cataracts caused by X-irradiation, such as described by Clark et al., *Invest. Ophthalmol.* 21:186, 1982, incorporated by reference herein; (2) cataracts induced by a high galactose diet (galactosemic cataracts), as described in Ishimoto et al., *Proc. Natl. Acad. Sci. U.S.A.* 76:4414–4416, 1979, incorporated by reference herein; (3) hypoglycemic cataracts in culture, described in Tanaka, *Invest. Ophthalmol. Vis. Sci.* 24:522–525, 1983, incorporated by reference herein; (4) cataract of a genetic origin, such as in the "Philly" mouse, described in Clark and Carper, *Proc. Natl. Acad. Sci. U.S.A.* 84:122–125, 1987, incorporated by reference herein, or "The Royal College of Surgeons" model; (5) cataract induced by administration of selenium, described in Bunce and Hess, *Exp. Eye Res.* 33:505–514, 1981, and reviewed in Shearer et al., *Curr. Eye Res.* 6:289–300, 1987, which are incorporated by reference herein; (6) and cataract caused by administration of streptozotocin.

The Radiation Model is widely regarded as the model for X-irradiation senile cataract. In general, irradiation is considered to accelerate the aging process and induce senility at a young age. The radiation model is convenient for experimental studies because the time of cataract formation can be controlled by controlling the dose of radiation. Irradiation has many side effects, in addition to cataract, and special care is necessary to maintain the animals. Tc changes during the early stages of cataract formation, and the opacity is associated with loss of soluble protein, hydration, and oxidation of proteins to form high molecular weight aggregates, which are characteristics of human senile cataract. The mature cataract forms approximately 100 days after irradiation.

A method for inducing radiation cataracts, described in detail in Clark et al., *Invest. Ophthalmol.* 21:186, 1982, is as follows: X-ray cataracts are produced in one eye of a New Zealand white rabbit by irradiating the eye with a single 2000 rad (85 kVp, 5 mAmp) dose when the animal is 5 to 6 weeks of age. Under these conditions a mature cataract develops in the irradiated eye 8 to 9 weeks after irradiation. The unirradiated contralateral lens has been found to receive less than 50 rad of irradiation and is used as a control. The animals may receive systemic administration of the drug, for example, or it may be applied topically. At measured intervals after irradiation and treatment, the lenses are observed for high molecular weight aggregates and/or cataractous opacification. The irradiated and unirradiated lenses may also be removed from the rabbit eyes. The lenses are placed immediately in silicone oil (Dow Corning 550) and kept at approximately 5° C. and the phase separation temperatures are then determined as described above.

On the Selenium Model, a mature cataract forms four or five days after a single administration of selenite. While the rapid formation of the cataract makes it a useful model for studies of the effects of PSI, it means that the initiating event is extreme and nonphysiological. Selenite is very toxic and slight overdoses kill the animals. Tc changes during the early stages of cataract formation, and the opacity is associated with increased levels of calcium, which is a common feature in many types of human cataract.

The Galactose Model is a model for diabetic cataract in humans. Continuous feeding of a diet that is high in galactose alters the activity of aldose reductase, an enzyme that is involved in diabetes. This model results in very sick animals, and their growth is severely inhibited by the galactose diet. The rate of cataract formation varies in different animals. Tc changes during the early stages of cataract formation and the opacity is associated with changes in glutathione levels, hydration, and formation of high molecular weight aggregates. The mature cataract forms 2-4 weeks after starting the diet.

The Streptozotocin Model is associated with the enzyme aldose reductase and is commonly employed as a model for human diabetes. In contrast to the galactose model, the cataract is induced by a single administration of streptozotocin, rather than continuous feeding. The drug is very toxic and must be administered carefully. The active form of the drug is an anomer so the exact composition of the drug must be carefully controlled. The response of individual animals to the streptozotocin varies widely, and 20%-25% of injected animals often did not form cataracts. Tc changes during the early stages of cataract formation, and the opacity is associated with changes in glutathione levels, hydration, and formation of high molecular weight aggregates. The mature cataract appears approximately 60 days after streptozotocin injection.

The Royal College of Surgeons (RCS) Model was developed by the Royal College of Surgeons as an animal model for hereditary cataract in humans. The cataract forms spontaneously 100-120 days after birth. Recently it has been shown that the hereditary defect is in the retina, not the lens, and the cataract forms secondary to retinal damage. Opacity associated with retinal disease is well known in humans, so the RCS rat remains an important model for human cataract formation. The opacity is associated with the oxidation of lens proteins induced by chemicals released from the abnormal retina.

The cataract models mentioned above can generally be classified under four basic categories or types: (1) oxidation, (2) diabetic (aldose reductase), (3) hereditary, and (4) calcium. Under the oxidation heading would fall the radiation and senile cataract models. The galactose and streptozotocin models fall under the diabetic category. The heriditary heading encompasses both the Philly and RCS cataract models. The calcium category includes the selenium cataract model.

Each of the four categories represents the formation of cataracts by a different mechanism. The compositions of the present invention, in addition to lowering Tc in vitro, prevent or delay the development of cataracts in at least two of the four categories mentioned above.

Using the methods described herein, one skilled in the art will be able to screen and identify compounds which may be useful in treating cataracts of diverse origin. Thus, the compounds will be observed to lower the phase separation temperature while inhibiting the formation of high molecular weight aggregates. Accordingly, the invention also concerns a method for screening phase separation inhibitors for use as anti-cataractic agents.

The compounds listed in Table 1 are exemplary of phase separation inhibitors of the present invention.

TABLE 1

| Phosphorylated Nucleotides | Sulfur-containing Compounds |
|---|---|
| adenosine triphosphate (ATP)* | |
| adenosine diphosphate (ADP)* | glutathione (GSSG)* |
| adenosine monophosphate (AMP)* | reduced glutathione (GHS)* |
| guanosine triphosphate (GTP)* | cysteine* |
| uridine triphosphate (UPT)* | dithiothreitol (DTT)* |
| Urea Derivatives | thiodhistidine |
| urea(thiocarbamyl acetamide)* | thiooctic amides |
| Vitamins | cystamine |
| alpha-tocopherol (vitamin E) | cystine |
| pyridoxine (HCl) | cystathione |
| pyridoxal (vitamin B6) | thiosulfates |
| ascorbic acid (vitamin C)* | thiouracil |
| Lipids | thiodiglycol |
| phosphoryl choline | (e.g. S-acetyle thiourea) |
| glycerol phosphoryl choline | sulfonylureas |
| Bile Salts | thioureds |
| glyceric acid | Amino Acids |
| thioglycolate | taurine* |
| taurodioleic acid | glycine* |
| glycosodeoxycholic acid | asparagine |
| Others | aspartic acid |
| biotin | glutamic acid* |
| pantothenic acid* | glutamine |
| pantonyl taurine | arginine |
| spermidine | custeomecusteome |
| putrescine | derivatives |
| carbachol | octopaniene |
| acrylosuccinimide | Sugar Derivatives |
| aminoethyl methacrylate | sorbitol* |
| aminoguanidine | glucose* |
| polyamine | galacitol* |

TABLE 1-continued histones
protamine

*Represents compounds found to reduce Tc in vitro

Following an initial screening to determine whether a specific compound reduces Tc in vitro, the compound would then be tested in at least two mechanistically distinct cataract models. If the compound delays or prevents the formation of cataracts in those models, the compound is suitable for treating cataracts of diverse origin within the methods of the present invention.

It has been discovered as part of the present invention that certain phosphorothioate compounds decrease the phase separation temperature of a lens, inhibit the formation of high molecular weight protein aggregates in the lens, and do not substantially affect the viscoelastic properties or color of the lens, Accordingly, these phosphorothioates may be employed to inhibit or prevent cataract development, and further may reverse the early stages of cataract which have developed prior to the initiation of therapy. Some representative phosphorothioate compounds useful in the present invention are described in U.S. Pat. No. 3,892,824, which is incorporated by reference herein, and includes, for example, S-2-(3-aminopropylamino) ethyl dihydrogen phosphorothioate, $NH_2(CH_2)_3NHCH_2CH_2SPO_3H_2$, also referred to as WR-2721. This compound, and hydrates or alkali metal salts thereof, may be synthesized according to the method described in U.S. Pat. No. 3,892,824 or other methods which will be known to those skilled in the art.

Another phosphorothioate compound preferred in the therapeutic and prophylactic methods herein is S-3-(amino-2-hydroxypropyl) phosphorpthioate, $NH_2CH_2CHOHCH_2SPO_3H_2$, also referred to as WR-77913. This compound, and hydrates or alkali metal salts thereof, may be synthesized according to the methods described in Piper et al., *J. Medical Chem.* 12:236–243, 1969, incorporated herein by reference, as well as by other processes which are known to those skilled in the art.

A third phosphorothioate useful in the present invention is S-2-(3-methylaminopropylamino) ethyl phosphothioic acid, $CH_3NH(CH_2)_3NHCH_2CH_2SPO_3H_2$, also known as WR-3689. This compound and hydrates or alkali metal salts thereof may be synthesized according to the method described in Piper et al., *J. Med. Chem.* 12:244–253, 1969, which is incorporated by reference herein, or by other methods known to those skilled in the art.

Accordingly, a phosphorothioate compound which may be employed in the methods herein may be selected from the group consisting of S-2-(3-aminopropylamino) ethyl dihydrogen phosphorothioate, S-3-(amino-2-hydroxypropyl) phosphorothioate, S-2-(3-methylaminopropylamino) ethyl phosphorothioate, and other phosphorothioates which decrease the phase separation temperature of lens cytoplasmic proteins and inhibit the formation of high molecular weight aggregates, and the hydrates and salts thereof.

For example, the phosphorothioate useful herein may be of the formula $RNHR_1SPO_3H_2$, wherein R is hydrogen, an alkyl group containing 1 to 6 carbon atoms, or the group $R_2NH(C_nH_{2n})-$, in which $R_2$ is hydrogen or an alkyl group containing 1 to 6 carbon atoms; $R_1$ is an optionally substituted alkylene group having from 1 to 6 carbon atoms; or hydrates and/or alkali metal salts thereof. Suitable alkali metal atoms include, for example, sodium, lithium or potassium. By "optionally substituted alkylene" is meant a branched or unbranched saturated hydrocarbon diradical of 1 to 6 carbon atoms, such as, for example:

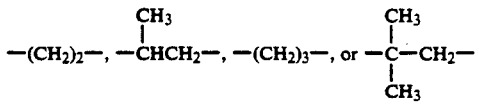

wherein the hydrocarbon chain is optionally substituted with 1 to 3 substituents, where examples of such substituted embodiments include hydroxy, halo, trifluoromethyl, alkoxy (—OR, where R is a lower alkyl having 1 to 3 carbon atoms, such as methyl, ethyl or propyl) and —$N(R_3R_4)$, where $R_3$ and $R_4$ are independently hydrogen or a lower alkyl having 1 to 3 carbon atoms, and the like.

Other species of phosphorothioates which may be useful herein are described in U.S. Pat. No. 3,892,824 and in *Chemical Protection Against Ionizing Radiation*, August 1984, Oregon State University, Appendix B, which are incorporated herein by reference.

The phosphorothioate compounds useful in the present invention may be screened and selected using the procedures herein described. The ability to lower the Tc may be tested in native lenses or lens homogenates. The ability to inhibit the formation of high molecular weight protein aggregates, as well as prophylactic or therapeutic efficacy, may be demonstrated in the appropriate animal models. For example, X-irradiation has been found to increase the phase separation temperature prior to causing the formation of high molecular weight aggregates, serious morphologic damage, and changes in lens permeability and lens transport. These changes are characteristic of many pathologic cataracts.

Another group of compounds, the succinimides and derivatives thereof, have also been discovered to lower the phase separation temperature and prevent the formation of high molecular weight aggregates and thus are useful in the methods of the present invention. Particularly preferred compounds of the invention include, inter alia, succinimide ($C_4H_5NO_2$), N-hydroxysuccinimide ($C_4H_5NO_3$), and ethosuximide (2-ethyl-2-methylsuccinimide, $C_7H_{11}NO_2$). These compounds have been found to strongly reduce the phase separation temperatures of solutions comprising concentrated bovine lens nuclear homogenate having a concentration of about 280 mg/ml. Succinimide has also been shown to reduce the phase separation temperature of lenses removed from whole rat eyes following incubation of the freshly extracted eyes in succinimide-containing solutions. Additionally, succinimide has been found to cause reversal of cataracts produced in vivo by sodium selenite.

A variety of succinimide compounds are known and may be synthesized using protocols familiar to those skilled in the art. Based on the teachings herein, one may screen such compounds for the ability to lower the Tc in vitro, and to inhibit the formation of high molecular weight aggregates in vivo. Appropriate in vivo efficacy and toxicity studies provide the artisan with succinimide compounds which may be formulated as pharmaceutically acceptable agents useful in preventing or treating cataracts.

Another class of compounds useful as pharmaceutical compositions for treating cataracts are members of the group pantethine, pantetheine, pantothenic acid, and panthenol. Pantethine has been demonstrated to be a phase separation inhibitor that prevents cataract produced by X-irradiation in vivo. These results are especially encouraging since pantethine, and pantethenic acid, from which it is derived, are approved for human use and widely available without restriction. Given the teachings herein, it is to be expected that one skilled in the art will be able to contemplate additional embodiments and derivations.

Still another class of compounds which have been found to lower the phase separation temperature and prevent formation of high molecular weight aggregates includes cysteamine.

Important elements for the successful use of the reagent compositions are the selection of the mode and dosage of administration as well as the timing of administration. Of course, the animal which is to be treated may also be an important consideration. For example, dosages may be higher in veterinary applications, such as for horses, dogs and cats, and may be more prolonged than might be possible or desirable with humans.

Preferably, the reagent composition should be applied before the formation of detectable levels of the high molecular weight protein aggregates, although it may also be applied up to and including the time that vision is noticeably impaired. It should also be applied as soon as possible after detection of any rise in phase separation temperature. Dosage is determined by the mode of administration. Administration of the active compounds and acceptable salts thereof can be via any of the accepted modes of administration for agents (or the pharmaceutically active metabolites thereof) which may be absorbed by the lens of the eye. These methods include topical, oral, parenteral and otherwise systemic or aerosol forms. Local or topical application in an acceptable physiological buffer may be preferred since a lower total dosage may be required.

Depending on the intended mode of administration, the compositions used may be in the form of solid, semi-solid, or liquid dosage forms, such as, for example, ointments, tablets, pills, capsules, powders, liquids, suspensions, or the like, preferably in unit dosage forms suitable for single administration of precise dosages. The compositions will include a conventional pharmaceutical carrier or excipient and an active compound or the pharmaceutically acceptable salts thereof and, in addition, may include other medicinal agents, pharmaceutical agents, carriers, adjuvants, etc. Of course, more than one pharmaceutically active reagent may be included in the compositions to achieve advantages not available from the separate administration of such reagents.

The amount of active compound administered will, of course, be dependent on the subject being treated, the stage of cataract development, the source of the cataract, the manner of administration and the judgment of the prescribing physician (or veterinarian). The amount required for effective prophylaxis or treatment may also be determined by measuring the decrease in phase separation temperature per mole. For in vivo application, it is necessary to decrease and maintain the phase separation temperature at less than body temperature while inhibiting the formation of high molecular weight aggregates.

For example, an effective dosage of a phosphorothioate composition, such as WR-77913, may be in the range of 10 to 2,000 mg/kg/day, preferably 50 to 1500 mg/kg/day if administered systemically. For an average 70 kg human, this would amount to 700 mg to 14 g/day, or preferably 3.5 to 10.5 g/day. Localized application via, e.g., topical preparations may reduce the dose accordingly.

Parenteral administration of the pharmaceutical reagent compositions is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol, or the like. In addition, if desired, the pharmaceutical compositions to be administered may also contain minor amounts of nontoxic auxiliary substances, such as wetting or emulsifying agents, pH buffering agents, and the like, such as, for example, sodium acetate, sorbitan monolaurate, triethanolamine oleate, etc.

For solid compositions, conventional nontoxic solid carriers include, for example, pharmaceutical grades of mannitol, lactose, starch, magnesium stearate, sodium saccharin, talcum, cellulose, glucose, sucrose, magnesium carbonate, and the like, may be used. Liquid pharmaceutically administrable compositions can, for example, be prepared by dissolving, dispersing, etc., an active reagent compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents, and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, Mack Publishing Co., Easton, Pa., 16th ed., 1982. The composition or formulation to be administered will, in any event, contain a quantity of the active compound(s) in an amount effective to inhibit the further development of cataracts in the subject being treated.

For oral administration, a pharmaceutically acceptable nontoxic composition is formed by the incorporation of any of the normally employed excipients, such as, for example, pharmaceutical grades of mannitol, lactose, starch, magnesium stearate, sodium saccharin, talcum, cellulose, glucose, sucrose, magnesium carbonate, and the like. Such compositions take the form of solutions, suspensions, tablets, pills, capsules, powders, sustained release formulations, and the like. Such compositions may contain 10%-95% active ingredient, preferably 25%-70%.

Another approach for parenteral administration employs the implantation of a slow-release or sustained-release system, such that a constant level of dosage is maintained. See, e.g., U.S. Pat. No. 3,710,795. Alternatively, a contact lens delivery system may be employed.

Preparation of an ophthalmic solution requires careful consideration of such factors as isotonicity value, the need for buffering agents, the need for a preservative and sterilization. Lacrimal fluid is isotonic with blood, having an isotonicity value corresponding to that of a 0.9% sodium chloride solution. Ideally, an ophthalmic solution should have this isotonicity value, but the eye can tolerate isotonicity values as low as that of a 0.6% sodium chloride solution and as high as that of a 2.0% sodium chloride solution without marked discomfort. Some ophthalmic solutions are necessarily hypertonic in order to enhance absorption and provide a concentration of the pharmaceutically active ingredient(s) strong enough to exert a prompt and effective action.

A boric acid vehicle which is preferred in some ophthalmic preparations has a pH slightly below 5.0. It may be prepared by dissolving 1.9 g of boric acid in sufficient water to make 100 mL of solution. A phosphate buffer system may also be employed, and adjusted for isotonicity provides a choice of pH ranging from 5.9 to 8.0. A pharmaceutical grade of methylcellulose (e.g., 1% if the viscosity is 25 centipoises, or 0.25% if 4000 centipoises) or other suitable thickening agents such as hydroxypropyl methylcellulose or polyvinyl alcohol occasionally are added to ophthalmic solutions to increase the viscosity and prolong contact of the drug with the tissue.

The following experimental examples are offered by way of illustration and not limitation.

EXAMPLE 1

Protection Against X-Irradiation Cataract by Phosphorothioate WR-77913

Protection by phosphorothioate WR-77913 against radiation-induced cataract formation in rats has been observed following intraperitoneal (i.p.) administration of drug (1160 mg/kg) 15 to 30 minutes before exposure to 15.3 Gy of Cs-137 whole head irradiation (presented by Menard et al. at the Chemical Modifiers for Cancer Treatement Conference, Clearwater, Fla. on Oct. 20-24, 1985, and reported in *Int. J. Radiation Oncology Biol. Phys.* 12:483-486, 1986. Control groups included irradiated, nonprotected animals, and sham-irradiated aging controls. Protection was documented photographically and by analysis of eye lens constituents. All nonprotected irradiated animals developed dense cataracts throughout the lens between 90-120 days post-irradiation, while WR-77913 protected animals developed minimal lens opacification through 200 days post-irradiation. Non-opacification in aging controls was seen.

Subsequent lens protein analysis by Lowry assay and size exclusion HPLC showed radioprotected and aging control animals were similar in protein content, distribution of total and soluble protein, and degree of lens hydration, as reported by Osgood et al., *Invest. Ophthalmol.* 27:1780-1784, 1986. This contrasted significantly with cataractous lenses on nonprotected animals. In cataractous lenses, the soluble protein concentration in the 25 to 43,000 dalton range was approximately 10% of that found in radioprotected or aging control lenses. Hydration was substantially higher in cataractous lens.

The following is a summary of the method and results obtained by systematic administration of the radioprotective compound WR-77913 prior to irradiation, showing prevention of radiation-induced cataractogenesis.

Methods and Materials

Animals: Male Sprague-Dawley rats, 7-9 weeks old, were housed separately in an environmentally controlled room with an artificial light cycle (6 a.m. to 6 p.m.). Three to five days acclimation was allowed prior to initiation of experiments. Food and water were provided ad libitum throughout the study. Irradiated animals were monitored daily for the first 10 days following initiation of experiments, and subsequently on an alternate day basis until the time of sacrifice.

Drug Preparation and Administration: Unlabeled S-3-(amino-2-hydroxypropyl) phosphorothioate was obtained from the Developmental Therapeutics Program, Division of Cancer Treatment, NCI. Drug purity was assessed by thin layer chromatography and melting point. Three hundred mg drug was dissolved per ml of filter sterilized calcium-magnesium free phosphate-buffered saline (0.13M PBS, pH 7.24) immediately prior to use and administered at a dose of 1160 mg/kg body weight. In control experiments, nonprotected, irradiated animals and aging control animals received an equal volume of PBS only.

Animal Irradiation: Gamma irradiation was performed with a Cs-137 teletherapy unit fitted with an 18×18 cm collimator. Irradiated animals received a single exposure of 15.3 Gy (0.63 Gy/min). Rats were unanesthetized and positioned in wedge-shaped lucite restraining devices so that the entire head was under the collimator. Dosimetry was measured with a 100 R ionization chamber. Sham-irradiated aging control animals were treated similarly to irradiated animals but without exposure to radiation.

Assessment of Eye Protection: The appearance of lenses from experimental groups was documented by whole eye and slit-lamp photographs, 154 days post-irradiation using a photo-biomicroscope. Rats were anesthetized with pentobarbital (30 mg/kg, i.p.) and the pupils dilated with 5% phenylephrine and 0.5% tropicamide.

Protein Analysis: Rats from each group were sacrificed in ether chambers up to 210 days after receiving treatments, and the eye enucleated and placed on ice. Lenses were dissected from the eye within 30 minutes and weighed. To study the content and molecular weight distribution of rat lens proteins, extracts were prepared by homogenizing individual lenses in 1 ml Wheaton homogenizers (Wheaton, Millwood, N.J.) with 0.5 ml of 0.10M sodium sulfate/0.02M potassium phosphate elution buffer (pH 6.9). The lense sulfate/0.02M potassium phosphate elution buffer (pH 6.9). The lense homogenate was transferred to microcentrifuge vials and the homogenizers rinsed twice with 0.25 ml of elution buffer. The total volume of 1.0 ml was vortexed for 5 seconds and centrifuged for 20 minutes at 17,000 rpm. The supernatant was decanted and filtered through 0.22 micron Millipore filters (Millipore, Beford, Mass.) and saved for protein analysis and size exclusion high performance liquid chromatography (HPLC). The pellet was resuspended in 0.1N NaOH. The amount of protein in the soluble and insoluble fractions was measured using the Lowry method standardized against bovine serum albumin.

A Perkin-Elmer Series 4 liquid chromatography module (Perkin-Elmer, Norwalk, Conn.), a Hewlett-Packard HP 1040A photodiode array spectrophotometer (Hewlett-Packard, Palo Alto, Calif.), and a TSK G3000SW, 30 cm by 7.5 mm column with a 10 cm guard column was used as the site-exclusion HPLC system. The buffer used for homogenization also served as the mobile phase with a flow rate of 0.5 ml/min. The injection volume for each sample was 10 microliters and absorbance was monitored at 280 nm. The TSK column was calibrated with known molecular weight standards.

FIG. 1 is a photographic representation of the protective effect that WR-77913 (PSI A) and pantethine (PSI B) had against cataract formation in X-irradiated rat lenses. Anterior and slit-lamp views of rat eyes from control, irradiated, and irradiated and drug-treated animals are shown 154 days after treatment. Control rat lenses remained transparent throughout the study. Irradiated rats which received no drug treatment developed moderate lenticular opacities within 90 days of receiving gamma radiation. Lens opacification progressed to mature cataracts by 120 days post-irradiation in all animals which received no WR-77913 or pantethine. Rats protected by WR-77913 or pantethine were noted to have only very slight lenticular opacities when photographed 154 days after irradiation. The appearance of the lens in the drug-treated rats remained stable until the animals were sacrificed at 210 days post-irradiation.

Lowry protein analysis demonstrated marked differences in total protein, soluble protein, and degree of hydration for cataractous lenses compared to radioprotected and aging control animals which were similar. For purposes of comparison the lens composition for each experimental group was normalized to the aging control group results expressed as percentages. In both radioprotected and aging control lenses, total protein comprised approximately 40% of the lens weight compared to 20% for the cataractous lenses. Of the total protein, the soluble fraction in aging control animals and radioprotected animals was 68% and 54%, respectively. In contrast, the soluble protein content in lenses of nonprotected rats comprised less than 5% of the total protein. Water accounted for approximately 80% for the cataractous lens weight compared to 60% of the lens weight from aging control and radioprotected animals. The lens weight from radio-protected and non-protected rats was not significantly different.

While the radioprotected lenses consistently showed less soluble protein that aging control lenses, the HPLC elution profile demonstrated the similarity between these experimental groups which contrasted with the findings from cataractous lenses. Both radioprotected and aging control elution curves demonstrated five similar peaks between 18 and 27 minutes. These peaks correspond to proteins with molecular weights of approximately 158,000, 43,000, 20,000, and 15,000 daltons. The elution profile of nonprotected cataractous lenses demonstrated sharp reduction in soluble proteins. The lens protein concentration in the 25-43,000 dalton range was 10% of that found in radioprotected or aging control lenses. There was no measurable soluble protein below 25,000 daltons. The hydration and dramatic increase in the ratio of insoluble to soluble protein in the cataract is due primarily to loss of soluble protein.

EXAMPLE 2

Decrease in Phase Separation Temperature by Phosphorothioates WR-77913 and WR-2721

The following example demonstrates the effect of two phosphorothioate compounds, WR-77913 and WR-2721, on the phase separation temperature of homogenates of lens tissue.

The measurement of dTc/dC, the difference in phase separation temperature produced by the reagent, is useful as a method for identifying potential reagents for preventing cataract in vivo.

Preparation of Homogenates: Native lens homogenate was prepared from lenses dissected from fresh calf eyes and cooled to 4'C. At this temperature, the lens nucleus opacifies and the transparent cortical layers were easily removed from the opaque nucleus. The nuclear samples were chopped into small pieces and a few drops of sodium azide (final concentration 0.04%) added to prevent bacterial contamination. The samples were then homogenized. Fifty or more lenses were used for each preparation of homogenate. This preparation has been shown to be very similar to native lens cytoplasm in physical, structural, and biochemical properties. The lens homogenates were used to test the effect of chemicals on Tc because the chemicals can be mixed uniformly in the cytoplasm at known concentrations. Studies using intact lenses must consider the partition coefficient in membranes, and the ability to penetrate into the cytoplasm in determining the final concentration of reagent in the cytoplasm.

Preparation of Experimental Samples: WR-77913 (S-3-amino-2-hydroxypropyl)phosphorothioate) and WR-2721 (S-2-(3-aminopropylamino) ethyl phosphorothioate) were supplied by the Developmental Therapeutics Program, Division of Cancer Treatment, NCI. The reagents were dissolved in distilled water and added to the homogenate by mixing one part of the solution with 9 parts homogenate. Controls were prepared with distilled water only. In all samples the concentration of homogenate was constant. The samples were gently homogenized to mix the additives with the homogenate. Preliminary studies showed that dilutions of 10% or less produced no additional background scattering and that the change in Tc was attributable to the addition of chemical reagents and was not simply the effect of dilution. The concentrations reported in the results were the final concentrations of the chemicals in the homogenates. The Tc values were measured over a concentration range between 0 mM and 50 mM for each reagent.

Measurement of Phase Separation Temperature (Tc): The intensity of the light transmitted through the samples was measured using a simple laser spectrometer. The relative transmittance was calculated as intensity, I, measured at any temperature, divided by the maximum intensity, $I_{max}$. Transmittance=$I/I_{max}$. The transmittance is measured over a range of increasing temperatures from 0° C. to 20° C. The samples were allowed to equilibrate at each temperature before recording the intensity.

The transition from Transmittance=0.0 (opaque) to Transmittance=1.0 (transparent) generally occurred over a narrow temperature range. The temperature at which Transmittance=0.5 was arbitrarily defined as Tc. The values of Tc obtained by this method were used in the determination of dTc/dC, a measure of the effect of each chemical on Tc.

Determination of dTc/dC: The effect of the chemical on Tc is defined as the change in Tc, with change in concentration of the chemical represented by dTc/dC. The Tc of the control, which contained only water, and the decrease in Tc produced by the chemical additives were determined. The mean decrease in Tc and the standard deviation were determined for each concentration. A linear regression was used to determine the best linear fit of the data and the correlation coefficient. The slope of the line was defined as dTc/dC.

Figure 2:
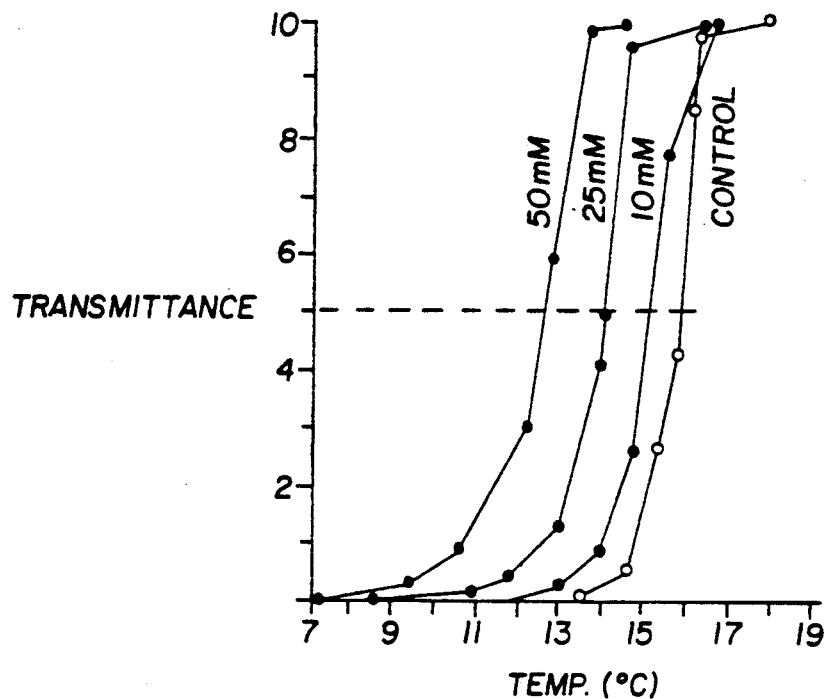
FIG. 2 is a graph of the transmittance of a cytoplasmic homogenate as a function of temperature (°C.) for samples containing 0.0 mM (control), 10 mM, 25 mM, and 50 mM galactose.

FIG. 2 depicts a concentration series used to determine the decrease in Tc at various concentrations of a reagent. In FIG. 2, the results were obtained using galactose, prepared essentially as described above for the phosphorothioates. In rats, a diet rich in galactose results in cataract formation, presumably via the aldose reductase pathway similar to that of the diabetic cataract. In mice, which do not form cataract when fed a diet rich in galactose, it has been discovered that the high galactose diet delays formation of cataracts after irradiation. These phenomena are distinct from the results shown in FIG. 2 which demonstrate the effect of galactose itself, not the metabolic products, on the phase separation temperature of the lens. The transmittance of the cytoplasmic homogenate was plotted as a function of the temperature of the lens. The transmittance of the cytoplasmic homogenate was plotted as a function of the temperature for samples containing 0.0 mM (control), 10 mM, 25 mM, and 50 mM galactose. The Tc for each sample is indicated in FIG. 2 by the intersection of each plot with the dashed horizontal line at Transmittance=0.5. The Tc was 15.6° C. in the control, 15.0° C. in the sample containing 10 mM galactose, 13.8° C. in the sample containing 25 mM galactose, and 12.4° C. in the sample containing 50 mM galactose. At temperatures above 17° C., all samples were completely transparent. The decrease in Tc relative to the control was −0.6° C. for 10 mM, −1.8° C. for 25 mM, and −3.2° C. for 50 mM galactose. Similar concentration series were used to measure the decrease in Tc produced by other reagents.

Figure 3:
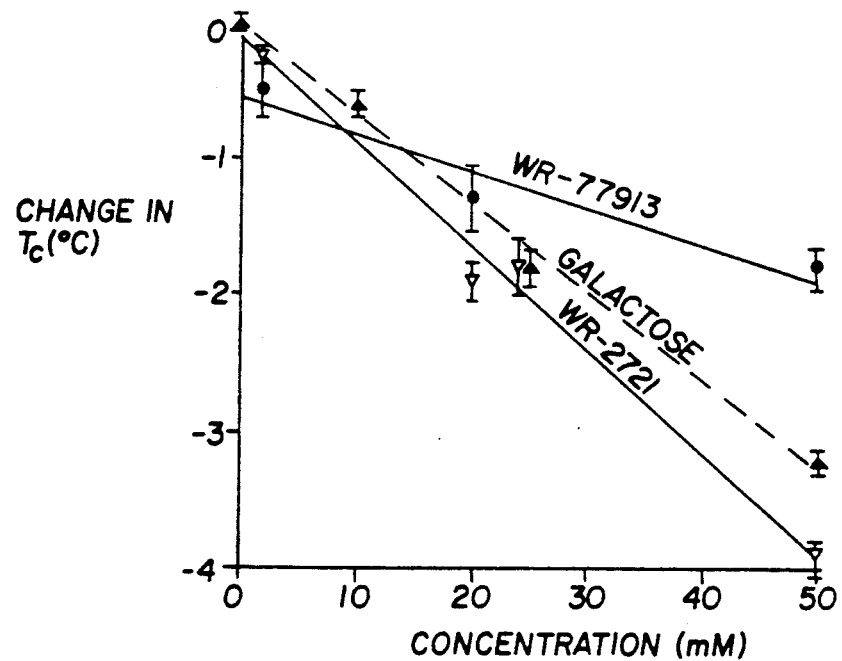
FIG. 3 is a graph of the change in phase separation temperature, Tc(°C.), versus concentration (0 to 50 mM) of galactose, WR-77913, and WR-2721.

FIG. 3 shows the decrease in Tc produced by galactose, WR-77913, and WR-2721 over the concentration range of 0 to 50 mM. The slopes of the regression lines through the data are the dTc/dC for each compound. dTc/dC was −65° C./mole for galactose, −28° C./mole for WR-77913, and −76° C./mole for WR-2721. The correlation coefficient was 0.997 for the galactose data, 0.800 for WR-77913, and 0.993 for WR-2721.

EXAMPLE 3

In Vivo Administration of WR-77913 Inhibits Streptozotocin-Induced Diabetic Cataracts WR-77913 was administered by i.p. injection 30 minutes prior to initiation of diabetic cataract by injection of 60 mg streptozotocin. The WR-77913 was administered as a single injection of 1160 mg/kg in PBS buffer. Mature cataracts were observed in the streptozotocin-treated animals approximately 42 days after injection. Mature cataracts were not observed in the WR-77913-treated animals.

In a second series of experiments, streptozotocin was dissolved in sterile sodium citrate, pH 5.0, to a concentration of 20 mg/ml. The streptozotocin solution was injected intravenously into the femoral vein of eight 5-week-old male Sprague-Dawley rats, such that each animal recieved a dose of 55 mg/kg of body weight. Half of the animals were injected i.p. with 1160 mg/kg of WR-77913 30 minutes prior to receiving streptozotocin.

Figure 4:
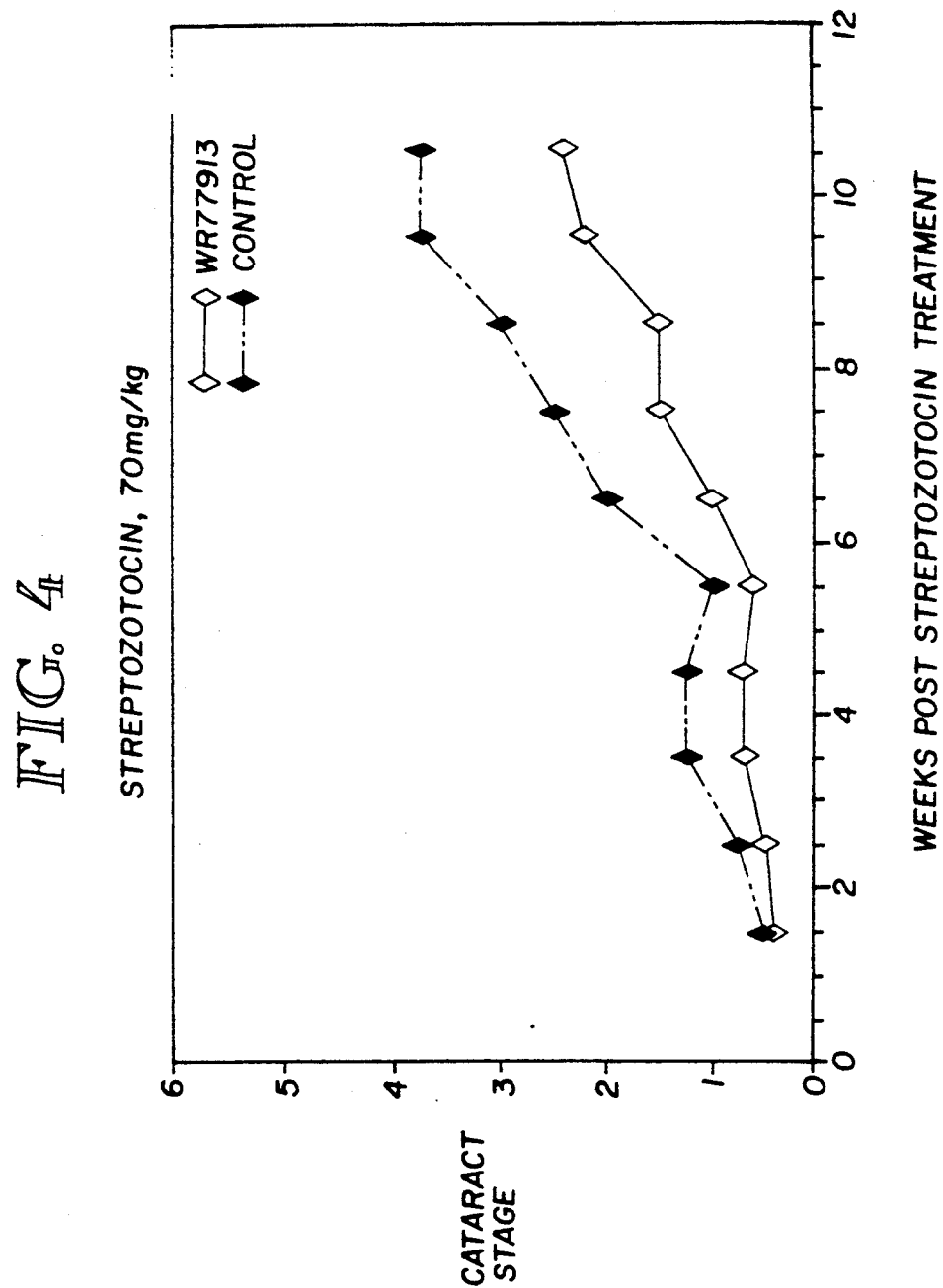
FIG. 4 is a graph of the inhibition of cataract development by WR-77913 compared to controls in animals with streptozotocin-induced diabetic cataract.

Animals were examined weekly with a slit-lamp biomicroscope for evidence of cataract development and staged according to the criteria of Sasaki et al., *Opthalmic Res.* 15:185–190, 1983, incorporated by reference herein. Under these criteria, the cataracts are classified as stages 1 through 6 on the basis of the appearance of the lens using a slit lamp. Stages 1 and 2 represent very slight changes in the lens without opacity. Stage 3 shows initial opacity. Stage 4 shows moderate opacity. Stage 5 is intense opacity involving much, but not all, of the lens. Stage 6 is a mature cataract in which the opacity involves the entire lens. The results of this experiment are shown graphically in FIG. 4.

EXAMPLE 4

In Vivo Administration of WR-77913 Inhibits Galactosemic Cataracts

WR-77913 was administered to rats that were induced to form galactosemic cataract. WR-77913 was administered by i.p. injection at a dose of 450 mg/Kg every 2 days after the galactosemic diet was initiated. Ten days after starting the galactosemic diet, cataract appeared in the rats not receiving the WR-77913. Mature cataracts were not observed in rats treated with WR-77913.

In another series of experiments, 23-day-old male Sprague-Dawley rats were fed a diet which consisted of 20% galactose by weight. On day one of the experiment, half the animals were injected i.p. with WR-77913 (580 mg/kg of body weight, in PBS). Animals were examined twice weekly for 32 days with a slit-lamp biomicroscope for evidence of cataract development and staged according to the criteria of Sasaki et al., supra. The results of this experiment are shown graphically in FIG. 5. Animals which received galactose only began to develop cataracts within one week of being started on the galactose diet. Within two weeks, the galactose-only animals all exhibited stage 3 cataracts, while the WR-77913-treated animals remained at stage 1. By day 32, the galactose-only animals all exhibited stage 5 cataract, while the WR-77913-treated animals remained at stage 1.

EXAMPLE 5

WR-77913 Inhibits Cataract Induced by X-Irradiation

WR-77913 was administered to X-irradiated animals 30 minutes following irradiation. The WR-77913 was administered as a single i.p. injection at a dose of 1160 mg/kg. After 90 days, cataract appeared in the animals which did not receive WR-77913. No cataract was observed in animals treated with WR-77913. These results indicate that WR-77913 and other phase separation inhibitors can be successfully used to prevent cataract when administered following the initiation of opacification.

EXAMPLE 6

Topical WR-77913 Inhibits Cataract Induced by X-Irradiation

WR-77913 was administered locally as eyedrops to the eyes of X-irradiated rats 60 minutes prior to X-irradiation. The eyedrops contained 600 mg/ml WR-77913 in PBS. The total amount of compound was about 0.5 ml, or about 1200 mg/kg. After 90 days, X-irradiation-induced cataracts appeared in the rats not receiving WR-77913, but no opacities were observed in the WR-77913-treated rats. These results indicated that local administration of WR-77913 and other phase separation inhibitors can be effective in preventing cataract.

EXAMPLE 7

WR-77913 Inhibition Cataract Induced by Selenium

Sodium selenite, dissolved in sterile saline to a concentration of 1.8 mg/ml, was injected subcutaneously into ten 14-day-old male Sprague Dawley rats such that each animal received a dose of 3.25 mg/kg of body weight. Five of the animals were also injected i.p. with WR-77913 (580 mg/kg, in PBS) approximately 15 minutes prior to selenium injection. Animals were examined over 21 days post-selenium injection three times per week with a slit-lamp biomicroscope for evidence of cataract development and staged 1-6 according to the criteria of Sasaki. Animals with a stage 3 or less were considered to have normal vision. The results of this experiment are shown graphically in FIG. 6. Animals which received selenite only and no treatment developed stage 5 (full nuclear) cataracts within one week of injection. Animals which were pretreated with WR-77913 did not progress beyond stage 2 during the study.

EXAMPLE 8

WR-2721 Inhibition of Cataract Induced by X-Irradiation

WR-2721 is an amino-phosphorothioate similar to WR-77913, which decreases the phase separation temperature, as shown in FIG. 3. A single i.p. injection of 500 mg/kg WR-2721 15 minutes prior to X-irradiation prevented formation of cataracts. The effect of WR-2721 is very similar to that of WR-77913 in the sense that it also prevented hydration, formulation of high molecular aggregates, and loss of soluble protein.

EXAMPLE 9

N-Hydroxysuccinimide Lowers the Phase Separation Temperature of the Lens

Both test lens and control lens were placed in aqueous solutions containing 0.1M phosphate buffer, 2% dimethyl sulfoxide (DMSO) at pH 7.0. The solution containing the test lense also contained a controlled amount of N-hydroxysuccinimide (NHS) ranging from 0-80 mM in concentration. After 48 hours incubation and subsequent dialysis of unbound NHS, the difference ($-Tc$) between the phase separation temperature of the test lens and the control was measured as a function of NHS concentration. The decrease in phase separation temperature ($-Tc$) in the calf lens is plotted in FIG. 7 as ordinate versus NHS concentration in mM plotted as abscissa.

Bovine lenses treated with NHS preparations for 40 hours in vitro have phase separation temperatures as much as 10° C. below that of a control lens, even following extensive dialysis of the lens, demonstrating the permanency of Tc suppression by NHS.

EXAMPLE 10

Topical NHS Lowers the Phase Separation Temperature of the Lens In Vivo

Fifteen-day-old Sprague-Dawley rats were used to test the effect of NHS on the decrease of Tc in vivo. Fifteen-day-old animals were selected because the normal Tc is above 30° C. at this age. 100 mM NHS in 0.154M phosphate buffer, pH 7.0, was applied to one eye of each rat over a 24-hour period. Phosphate buffer alone was applied to the opposite eye as a control. The solutions were applied approximately every 30 minutes from 4 p.m. to 9 p.m., and again every 30 minutes from 7:30 a.m. to 4 p.m. the next day to the eyes as drops (containing approximately 6 mg), using a syringe (a total of approximately 116 mg). At 4 p.m., 24 hours after beginning the experiment, all three rats were sacrificed and the lenses were removed and placed in silicon oil. The Tc was measured in each lens:

|  | Tc (°C.) | | |
|---|---|---|---|
|  | Control Eye (no NHS) | NHS | Tc |
| Rat 1 | 33.5 | 32.0 | −1.5 |
| Rat 2 | 39.0 | 36.2 | −2.8 |
| Rat 3 | 38.5 | 35.5 | −3.0 |

EXAMPLE 11

In Vitro Reduction of Phase Separation Temperature Using Succinimide and Ethosuximide Concentrated bovine nuclear homogenate was assayed to be approximately 280 mg/ml. Solutions of succinimide and ethosuximide in phosphate buffer (0.1M, pH 7) were prepared by having concentrations of 1.2, 0.8, 0.6, 0.4, 0.2, 0.08, and 0.04M. Ten microliters of the succinimide solutions were added to a first set of 90 microliter samples of the concentrated nuclear homogenate. Ten microliters of the ethosuximide solutions were added to a second set of 90 microliter samples of the concentrated nuclear homogenate. The resulting solutions were found to be about 252 mg/ml, and the resultant succinimide and ethosuximide concentrations were about 120, 80, 60, 40, 20, 8, and 4 mM. A control sample was prepared by adding 10 microliters of buffer to 90 microliters of concentrated nuclear homogenate.

The samples were allowed to stand for about 4 hours and the Tc values for each were then determined. Both the succinimide and the ethosuximide were found to decrease the Tc in each of the homogenate samples. The change in Tc as it related to the concentration of the reagent was found to be the same for both succinimide and ethosuximide. This relationship is given as:

$$\frac{dTc}{d[C]} = 53.3° \text{ C./Mole}$$

Figure 8B:
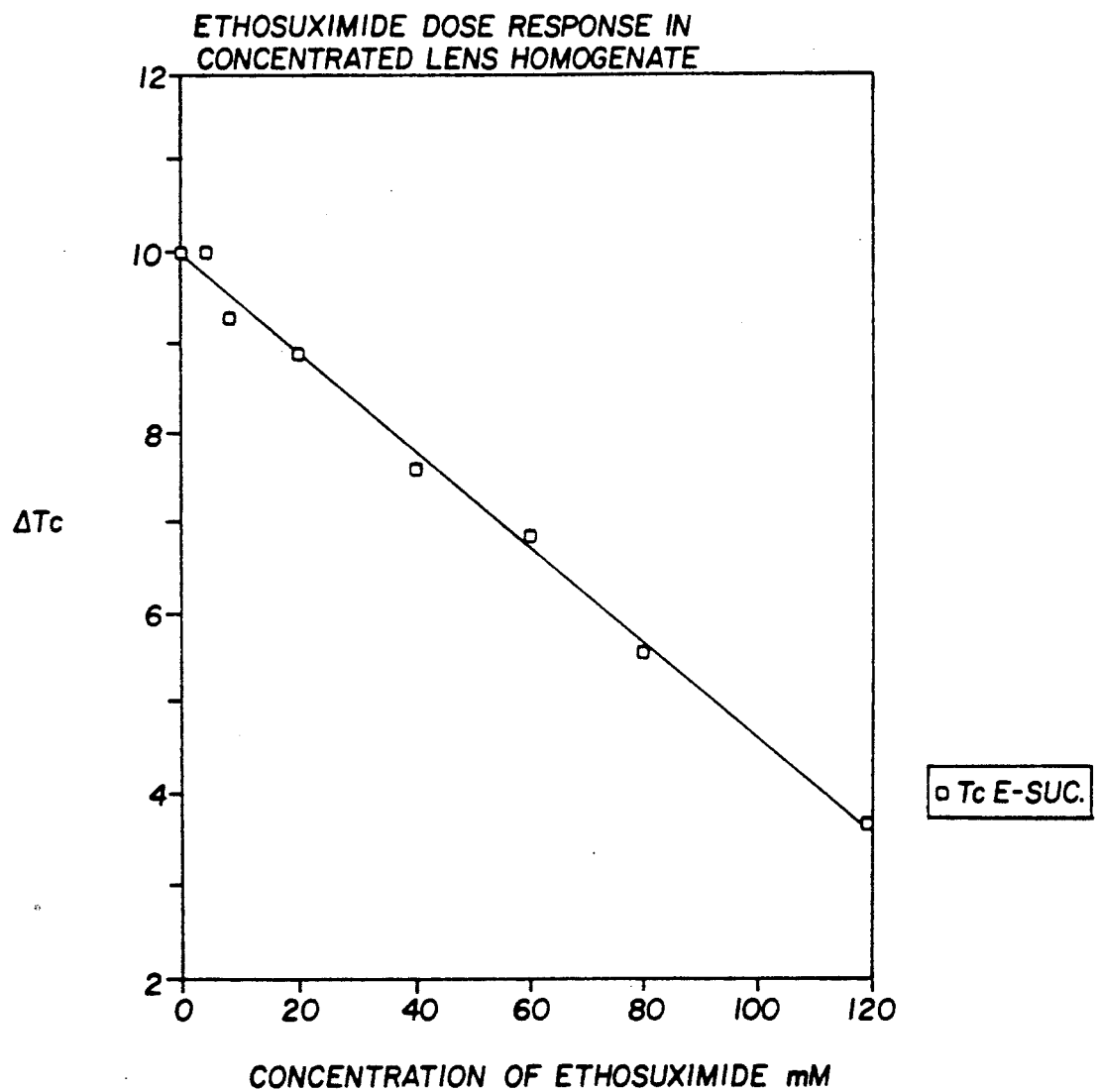

Data for succinimide in which the change in Tc is plotted against reagent concentration is given in FIG. 8(a). Data for ethosuximide in which the change in Tc is plotted against reagent concentration is given in FIG. 8(b).

EXAMPLE 12

Reduction of Phase Separation Temperature in Whole Rat Eyes Using Succinimide Freshly removed rat eyes were placed in solutions of physiological saline which contained 0, 100, 200, and 300 mM succinimide. The eye were allowed to incubate for 24 hours at 4° C. The lenses were then removed and Tc values were determined. The change in Tc as it relates to the succinimide concentration was determined as:

$$\frac{dTc}{d[C]} = 55.6° \text{ C./Mole}$$

Figure 9:
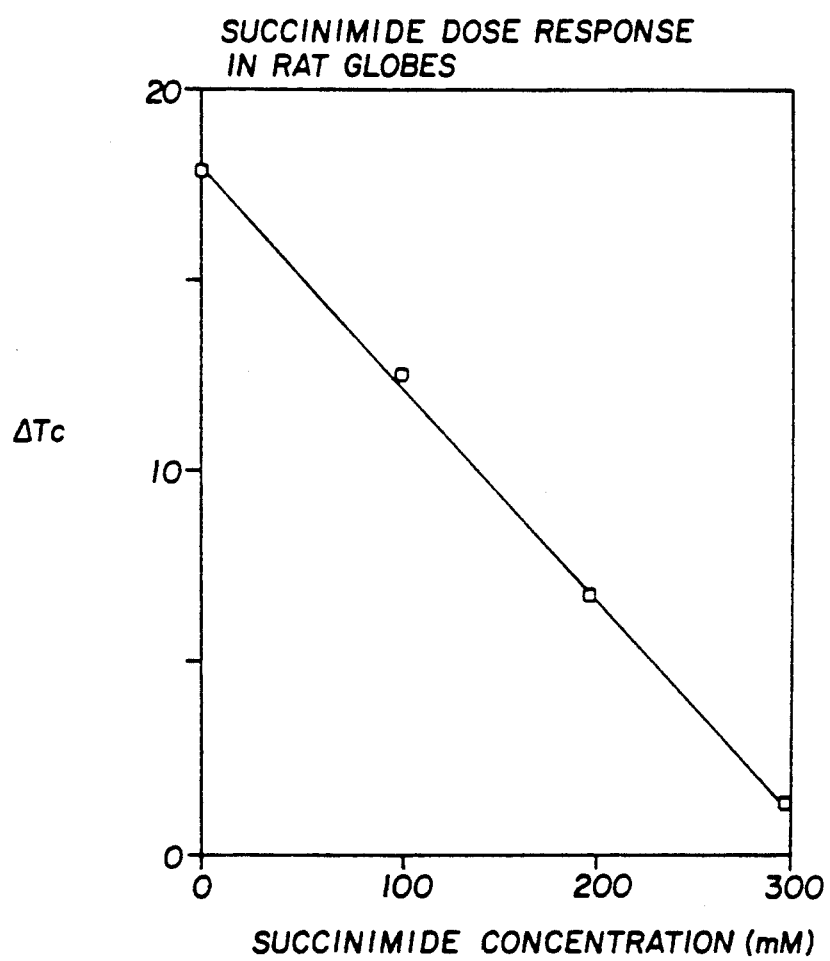
FIG. 9 is a graph of the change in phase separation temperature, Tc(°C.), versus concentration of succinimide applied to freshly removed whole rat eyes.

Data in which the change in Tc is plotted against reagent concentration is given for this example in FIG. 9.

EXAMPLE 13

In Vitro Reversal of Selenium Cataract With Succinimide

Sodium selenite was administered to 15-day-old Sprague-Dawley rats to induce cataracts. After 4-5 days, the eyes in which the selenite-induced cataracts had formed were removed by removing the complete eye globes from each animal. Each globe was subsequently immersed in a 300 mM/1 succinimide solution. In the presence of succinimide, the cataract in the lens of each eye disappeared. Thus, the method of this example provided an actual reversal of in vivo cataracts.

EXAMPLE 14

Reduction of Phase Separation Temperature In Vivo Using Succinimide

In two animals, a 1 molar solution of succinimide in phosphate buffered saline, PBS, was administered as eye drops to one eye and PBS alone was administered to the opposite eye as a control. After 2 hours, the lenses were removed and the Tc in each lens was measured.

Figure 10:
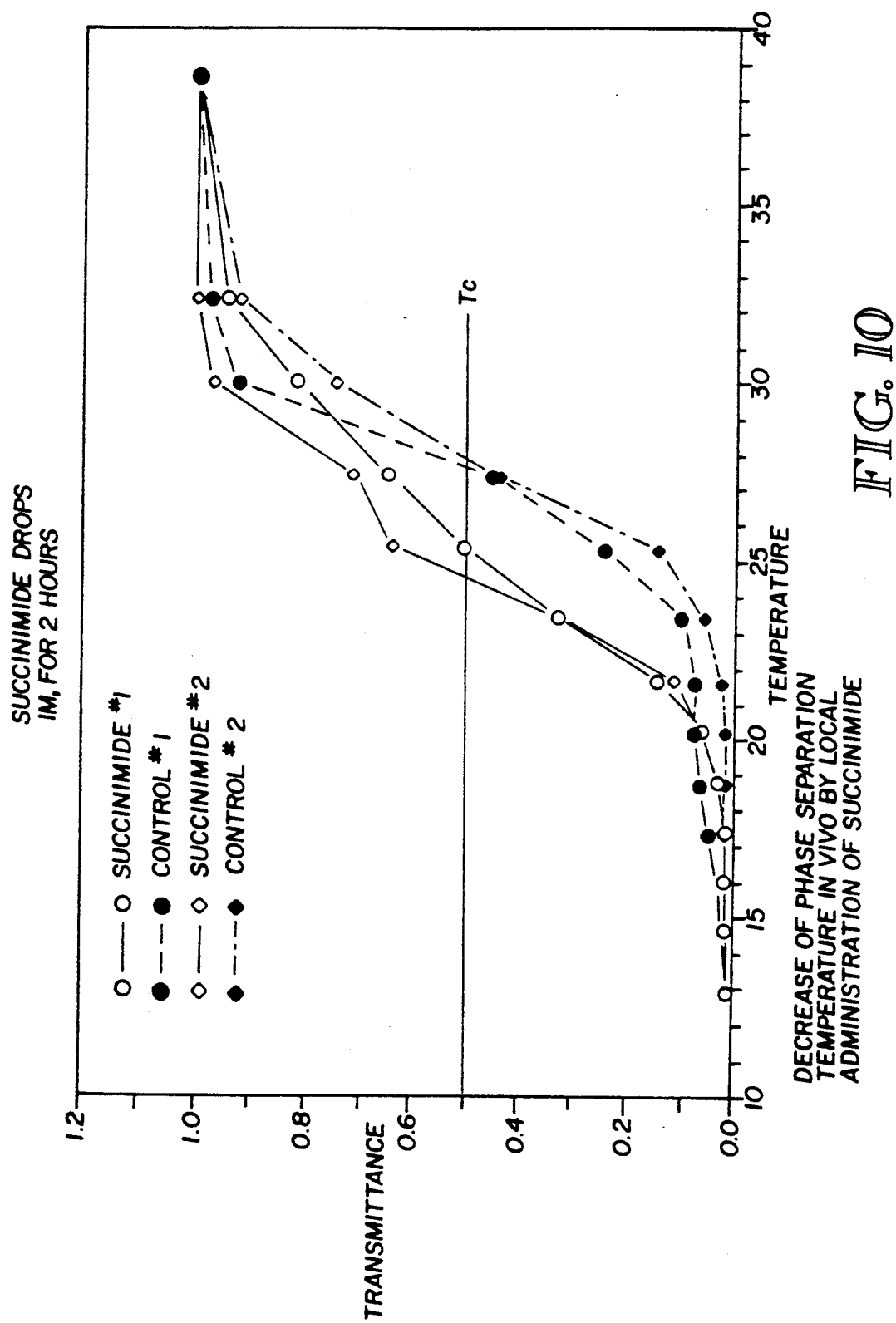
FIG. 10 is a graph of lens transmittance versus temperature (°C.) determined following in vivo topical applications of succinimide.

The Tc in the lenses treated with succinimide was found to be about 3.5° C. lower than the Tc of lenses treated with the PBS control. These results demonstrated that topical administration of a phase separation inhibitor such as succinimide can effectively introduce the reagent to the interior of the lense and subsequently lower the phase separation temperature of lens proteins. A plot of lens transmittance versus lens temperature for both succinimide-treated and control lenses is presented in FIG. 10.

EXAMPLE 15

In Vitro Reduction of Phase Separation Temperature Using Pantethine

Concentrated bovine nuclear homogenate was assayed to be approximately 280 mg/ml. A solution of pantethine in phosphate buffer (0.1M, pH 7), was prepared having concentrations of 0.50, 0.25, 0.20, 0.10, and 0.05 Molar. Ten microliter samples of the pantethine solutions were added to a second set of 90 microliter samples of concentrated bovine nuclear homogenate. A control sample was prepared by adding 10 microliters of buffer solution to 90 microliters of concentrated bovine nuclear homogenate.

Figure 11:
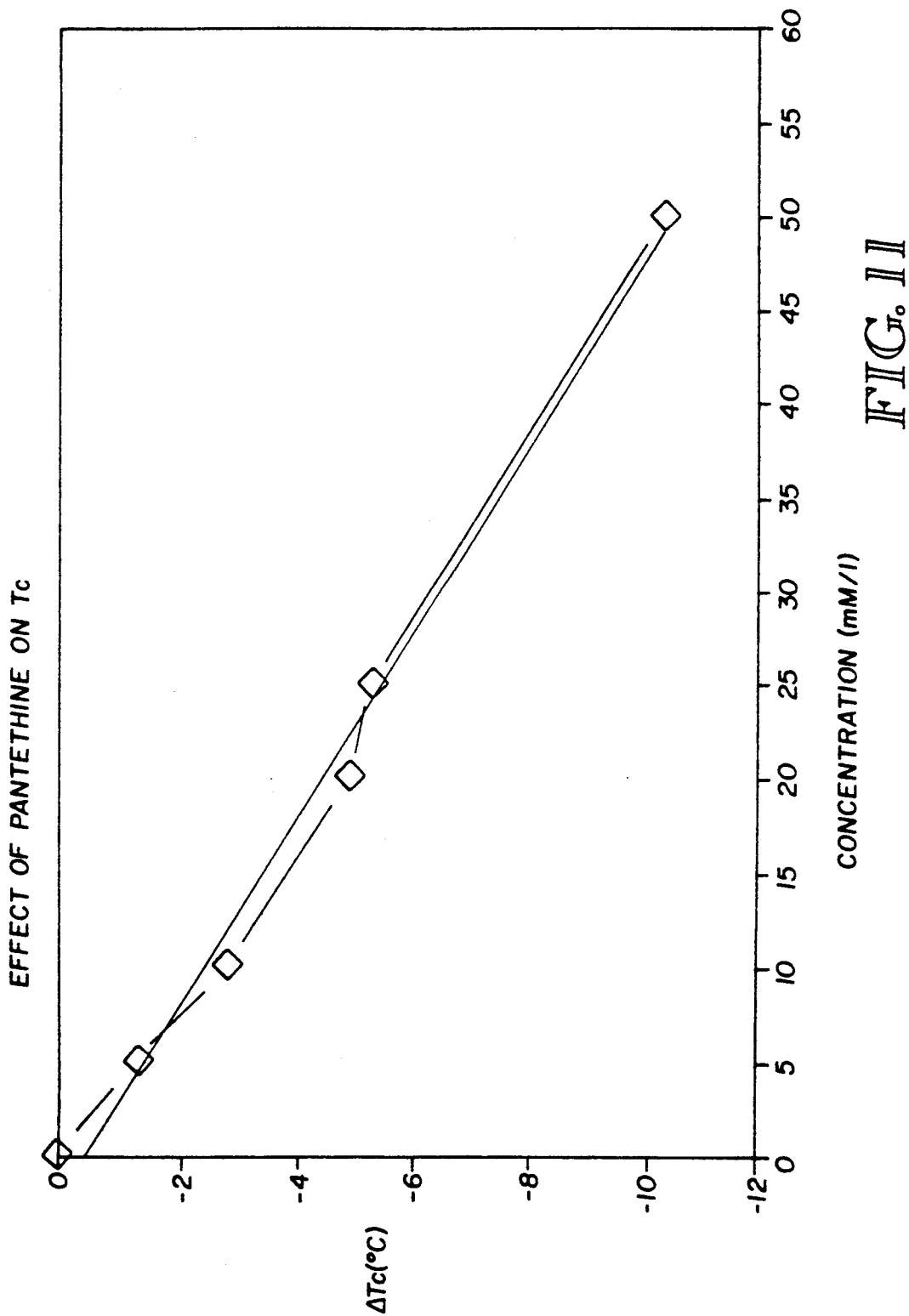
FIG. 11 is a graph of the change in phase separation temperature, Tc(°C.), versus concentration of pantethine in vitro.

The samples were allowed to stand for 24 hours and the Tc values for each were determined. The results indicated that pantethine is a strong phase separation inhibitor, lowering the phase separation temperature approximately 210° C./Mole. Data for pantethine, in which the change in Tc is plotted against reagent concentration, is given in FIG. 11.

EXAMPLE 16

WR-77913 Inhibition of X-Irradiation Cataract In Vivo

A single intraperitoneal (i.p.) injection of approximately 1160 mg/kg WR-77913 (PSI A) 15 minutes prior to irradiation prevented formation of cataracts produced by X-rays in Sprague-Dawley rats. These results can be seen in FIG. 1, previously described.

EXAMPLE 17

Pantethine Inhibition of X-Irradiation Cataract In Vivo

A single i.p. injection of approximately 600 mg/kg pantethine (PSI B) 15 minutes prior to irradiation prevented formation of cataracts produced by X-rays in Sprague-Dawley rats. These results can be seen in FIG. 1, previously described.

EXAMPLE 18

WR-77913 Inhibition of Selenite Cataract In Vivo

Figure 12:
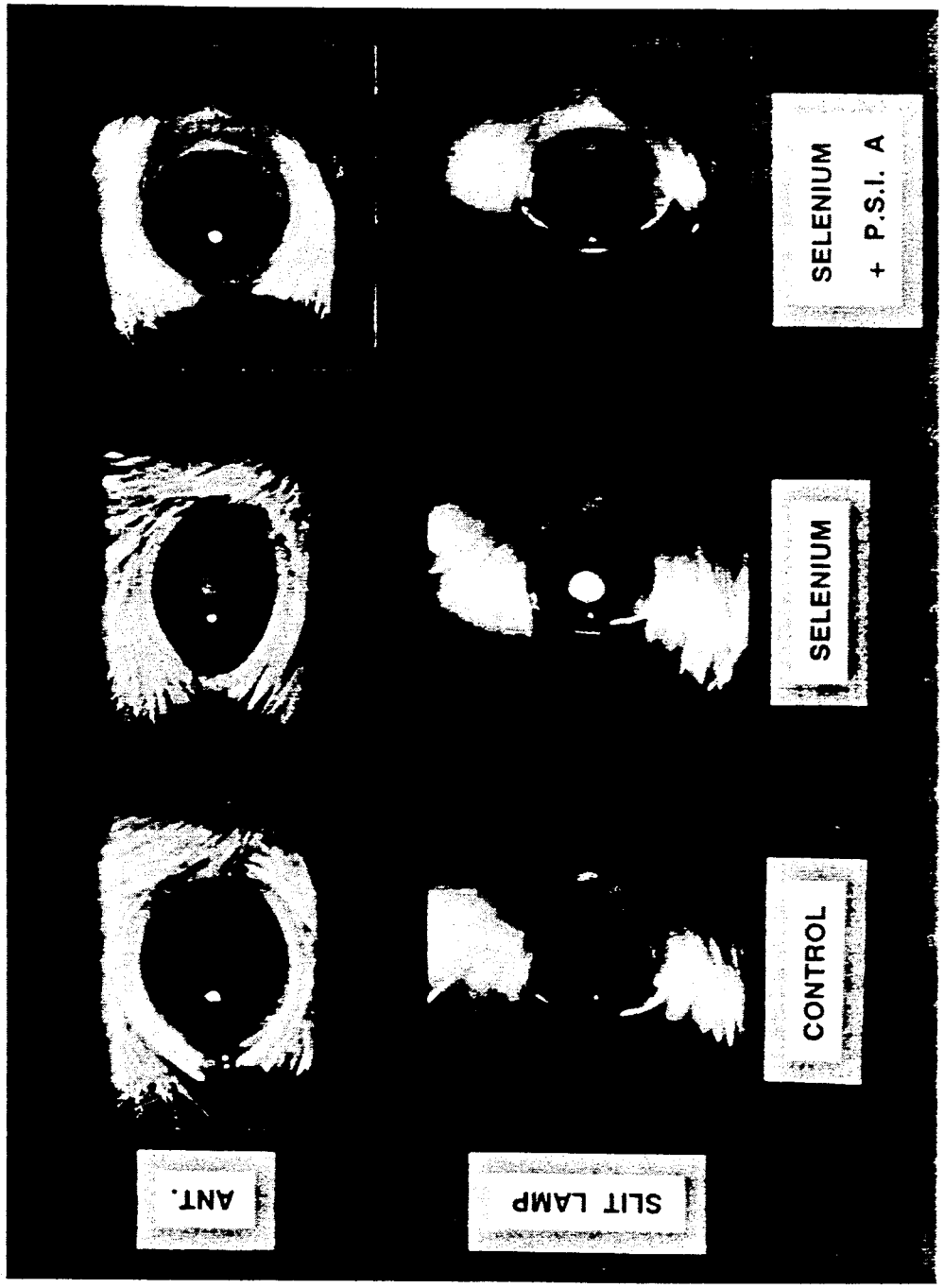
FIG. 12 is a photograph of control rat eyes compared to cataractous rat eyes and rat eyes treated with PSIA prior to selenium injection.

FIG. 12 illustrates WR-77913 (PSI A) as an effective inhibitor of selenite cataract. The photographs were taken approximately 7 days after injection of selenite. PSI A was administered as a single i.p. injection of approximately 600 mg/kg 15 minutes prior to selenite injection.

EXAMPLE 19

Pantethine Inhibition of Selenite Cataract In Vivo

Figure 13:
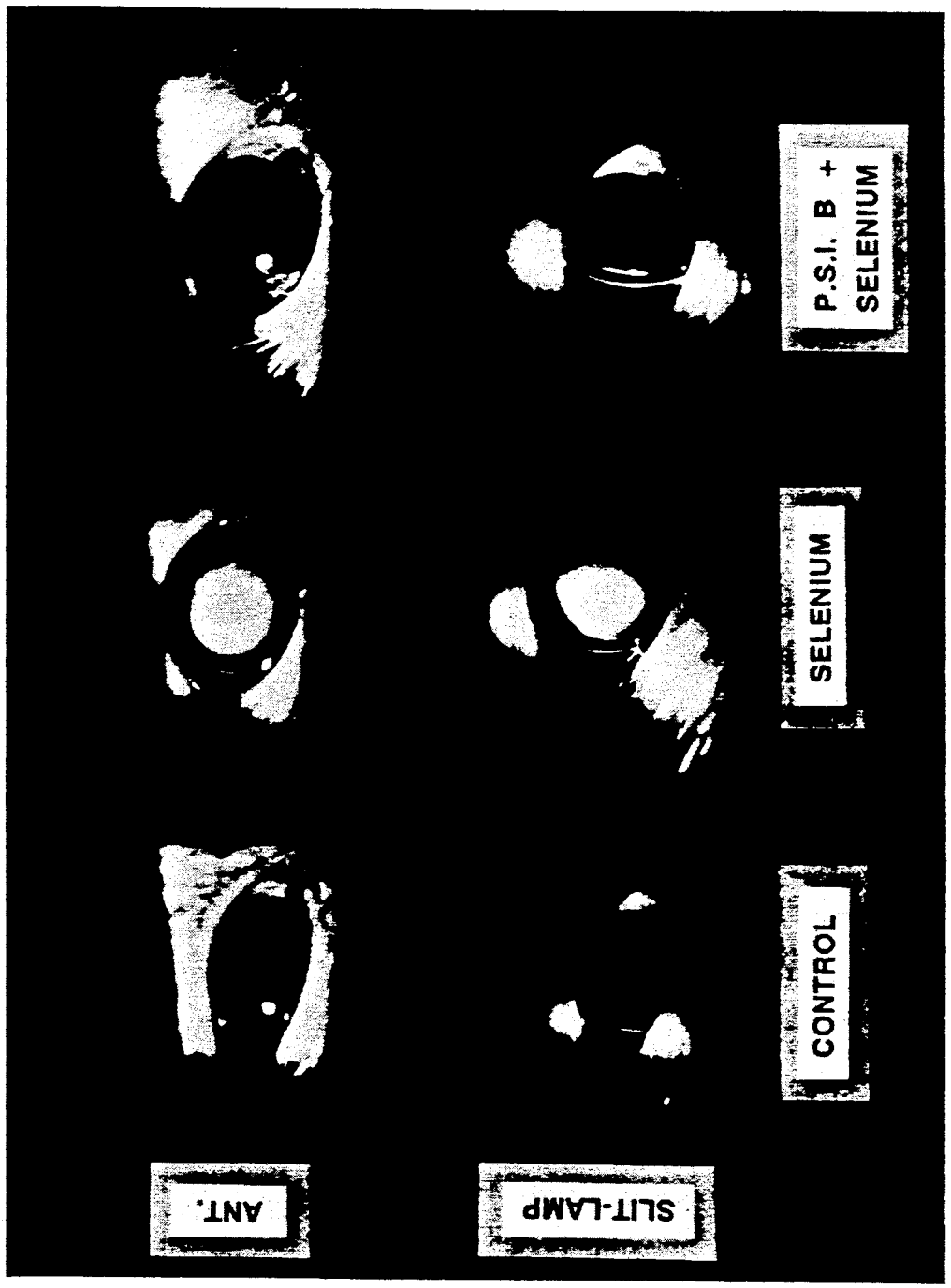
FIG. 13 is a photograph of control rat eyes compared to cataractous rat eyes and rat eyes treated with PSI B prior to selenium injection.

The effect of pantethine (PSI B) upon selenite cataract is depicted in FIG. 13. The photographs were taken approximately 14 days after injection of selenite.

EXAMPLE 20

WR-77913 Inhibition of Galactose Diet Cataract In Vivo

Figure 14:
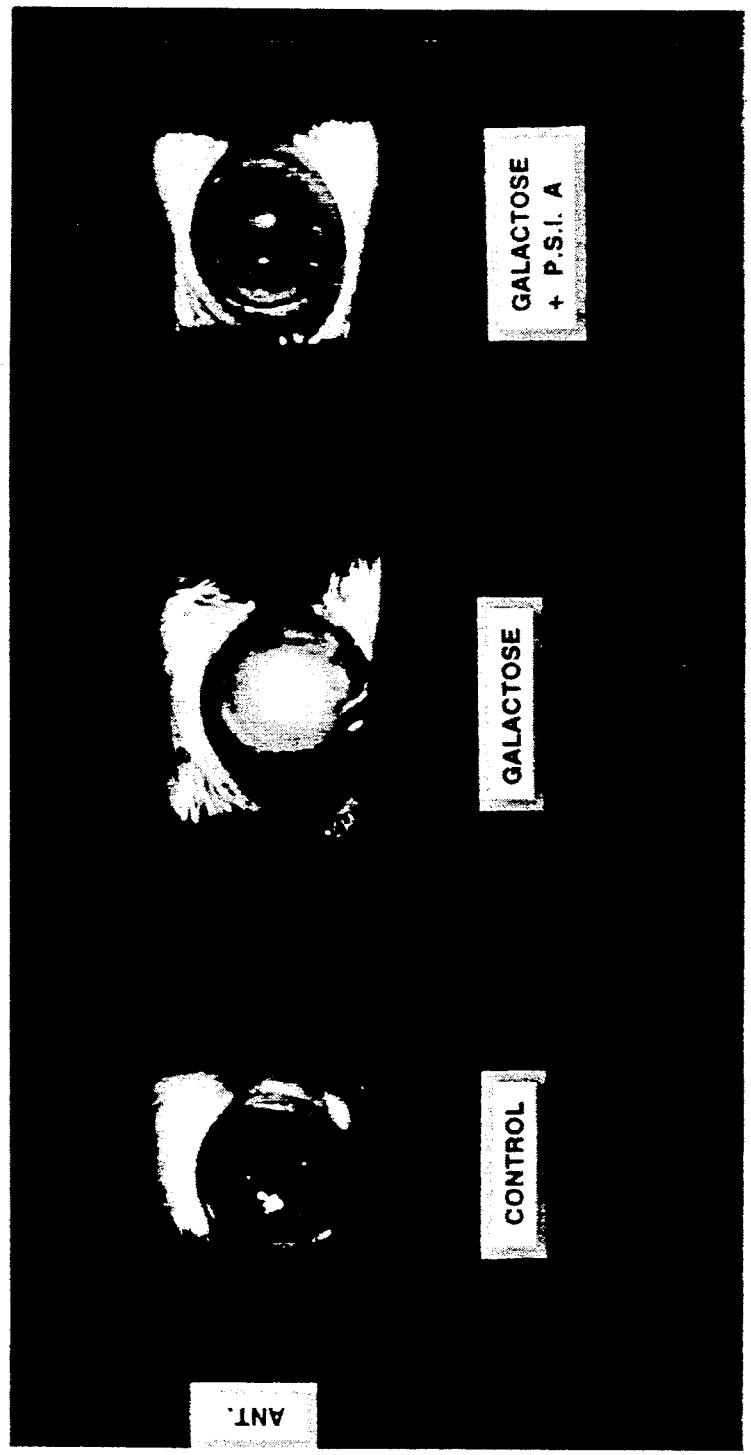
FIG. 14 is a photograph of control rat eyes compared to cataractous rat eyes and rat eyes treated with PSI A in high galactose diet rats.

FIG. 14 illustrates inhibited cataract formation by WR-77913 (PSI A) on high galactose diet cataract. The photographs were taken approximately 3 weeks after starting the diet. PSI A was administered as a 300 mg i.p. injection every other day for 3 weeks.

EXAMPLE 21

WR-77913 Inhibition of Streptozotocin Cataract In Vivo

Figure 15:
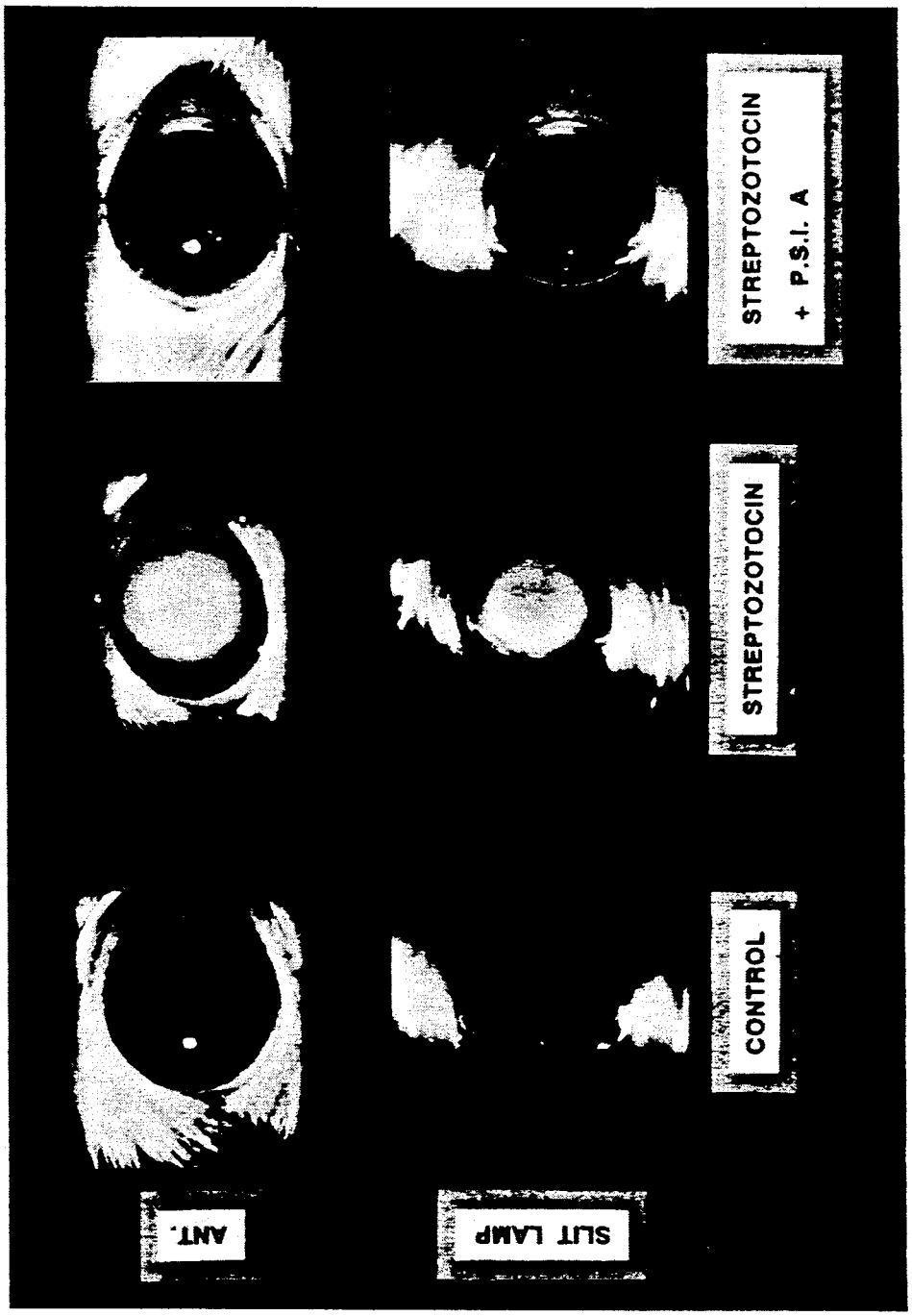
FIG. 15 is photograph of control rat eyes compared to cataractous rat eyes and rat eyes treated with PSI A prior to streptozotocin injection.

WR-77913 (PSI A) prevented cataract in the majority of animals injected with streptozotocin. This is illustrated in FIG. 15. The photographs were taken approximately 70 days after injection of streptozotocin. PSI A was administered as a single i.p. injection of approximately 1160 mg/kg 30 minutes prior to injection with streptozotocin.

EXAMPLE 22

Pantethine Inhibition of RCS Cataract In Vivo

Figure 16:
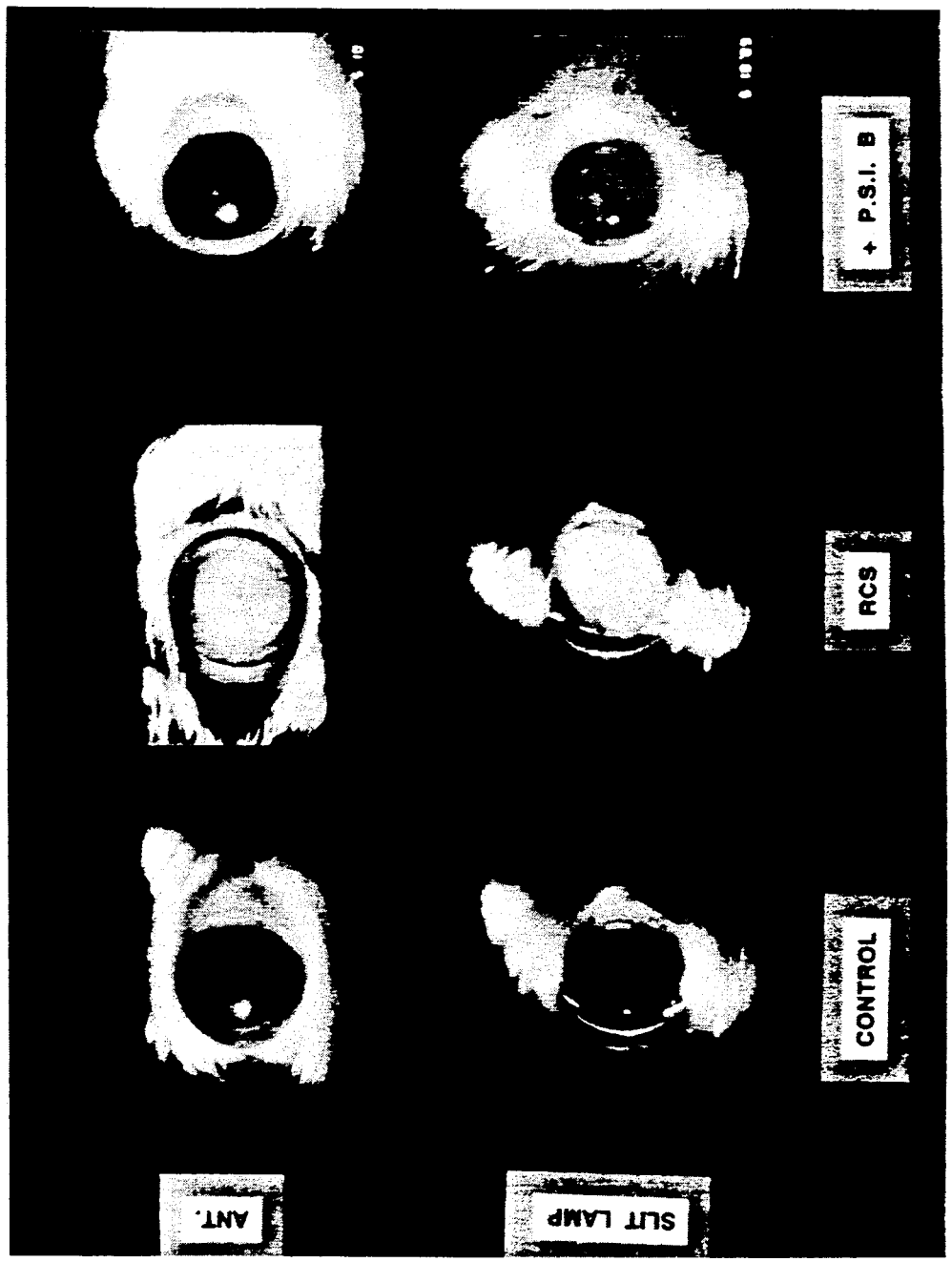
FIG. 16 is a photograph of control rat eyes compared to cataractous rat eyes and rat eyes treated with PSI B in RCS rats.

FIG. 16 depicts the inhibitory effect of pantethine (PSI A) on RCS cataract. The photographs were taken approximately 6 months after birth of the RCS animals. Eighty percent of the RCS animals which were not administered PSI B formed cataracts. PSI B protected 75% of the animals. PSI B was administered as a 300 mg i.p. injection once a week for the life of the animal.

EXAMPLE 23

In FIGS. 17-22, each vertical bar represents the cataract stage in a single animal.

Figure 17:
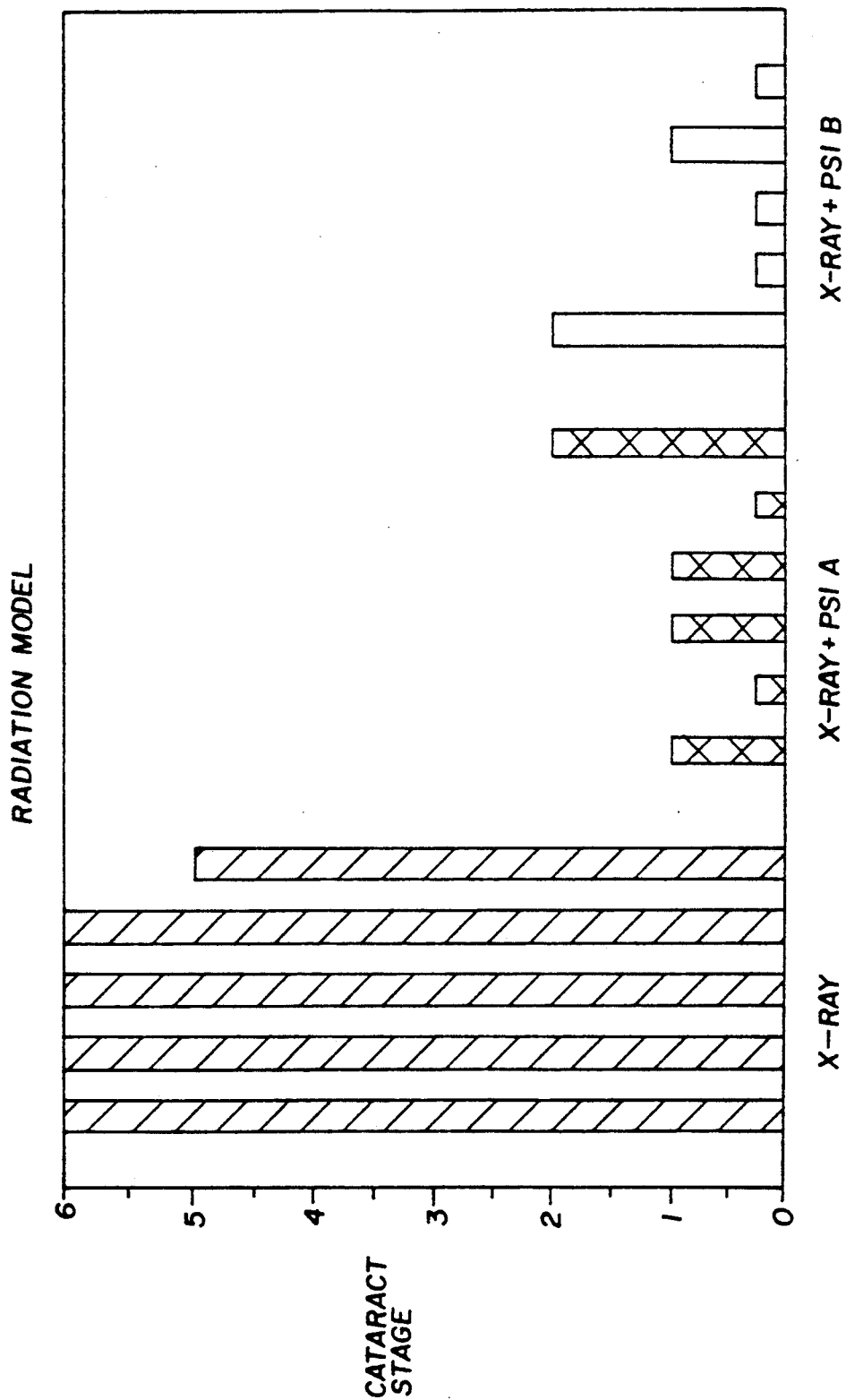
FIG. 17 is a graph of the effect of PSI A and B on radiation induced cataract.

FIG. 17 illustrates the effect of PSI A on X-irradiated cataract. In most irradiated animals, mature (stage 6) cataracts were observed 150 days after animals were irradiated. Animals treated with PSI A did not opacify.

Figure 18:
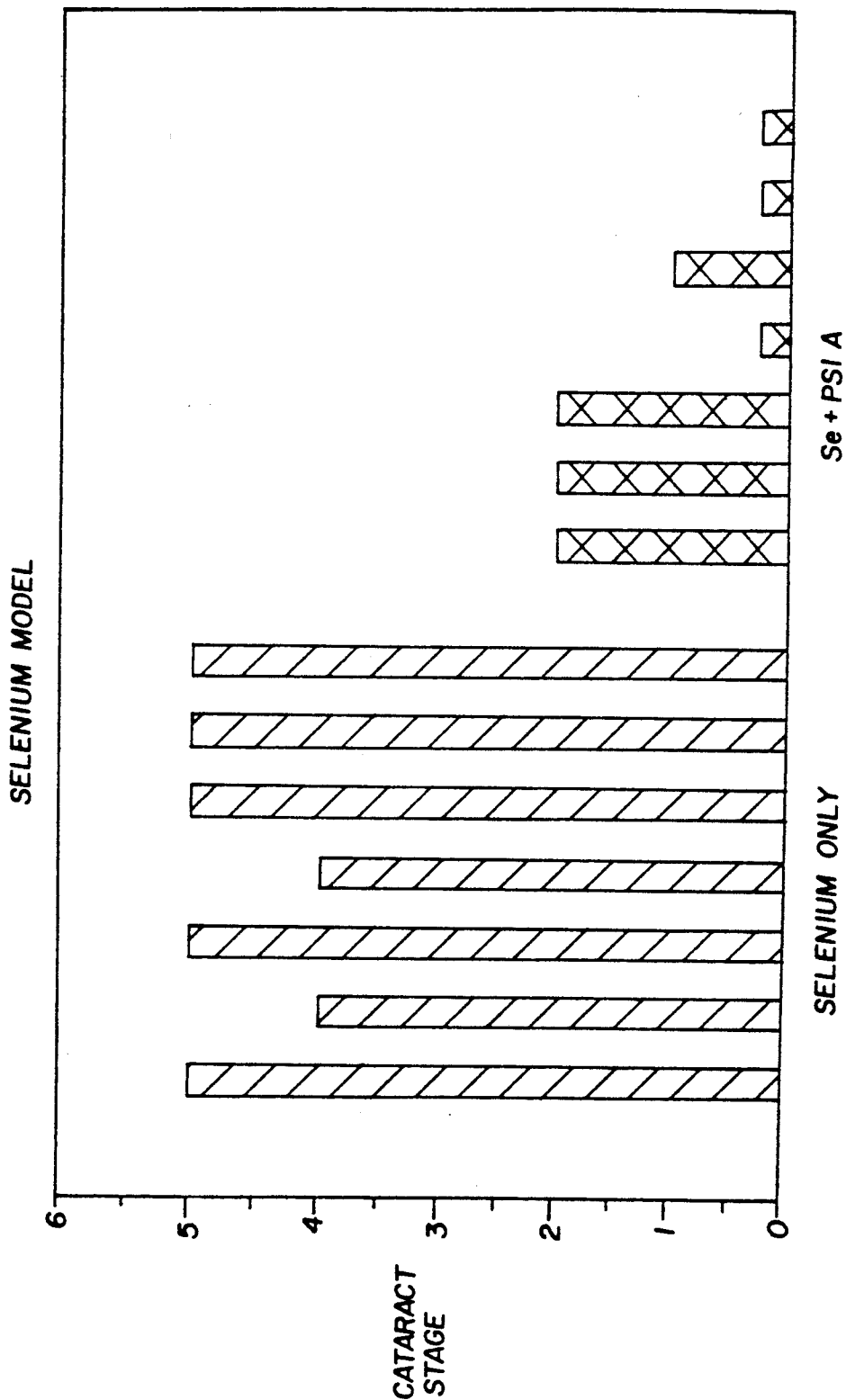
FIG. 18 is a graph of the effect of PSI A on selenium induced cataract.

FIG. 18 depicts the effect of PSI A on selenium cataract. PSI A inhibited cataract formation in all animals injected with selenium. In the absence of PSI, all animals formed mature cataracts 4 days after administration of selenium.

Figure 19:
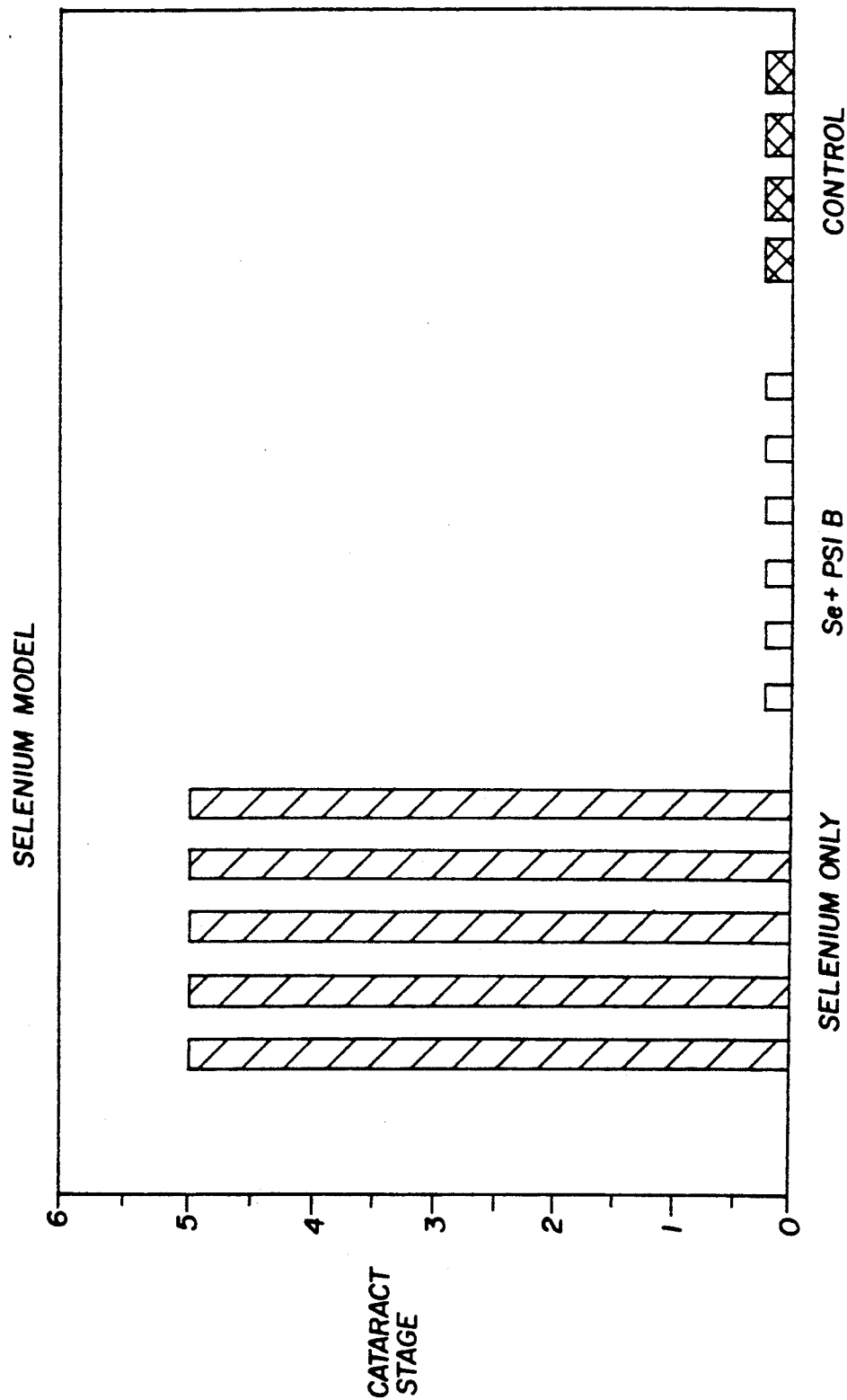
FIG. 19 is a graph of the effect of PSI B on selenium induced cataract.

FIG. 19 shows the effect of PSI B on selenium cataract. PSI B inhibited cataract formation in all animals injected with selenium. In the absence of PSI, all animals formed mature cataracts 5 days after administration of selenium.

Figure 20:
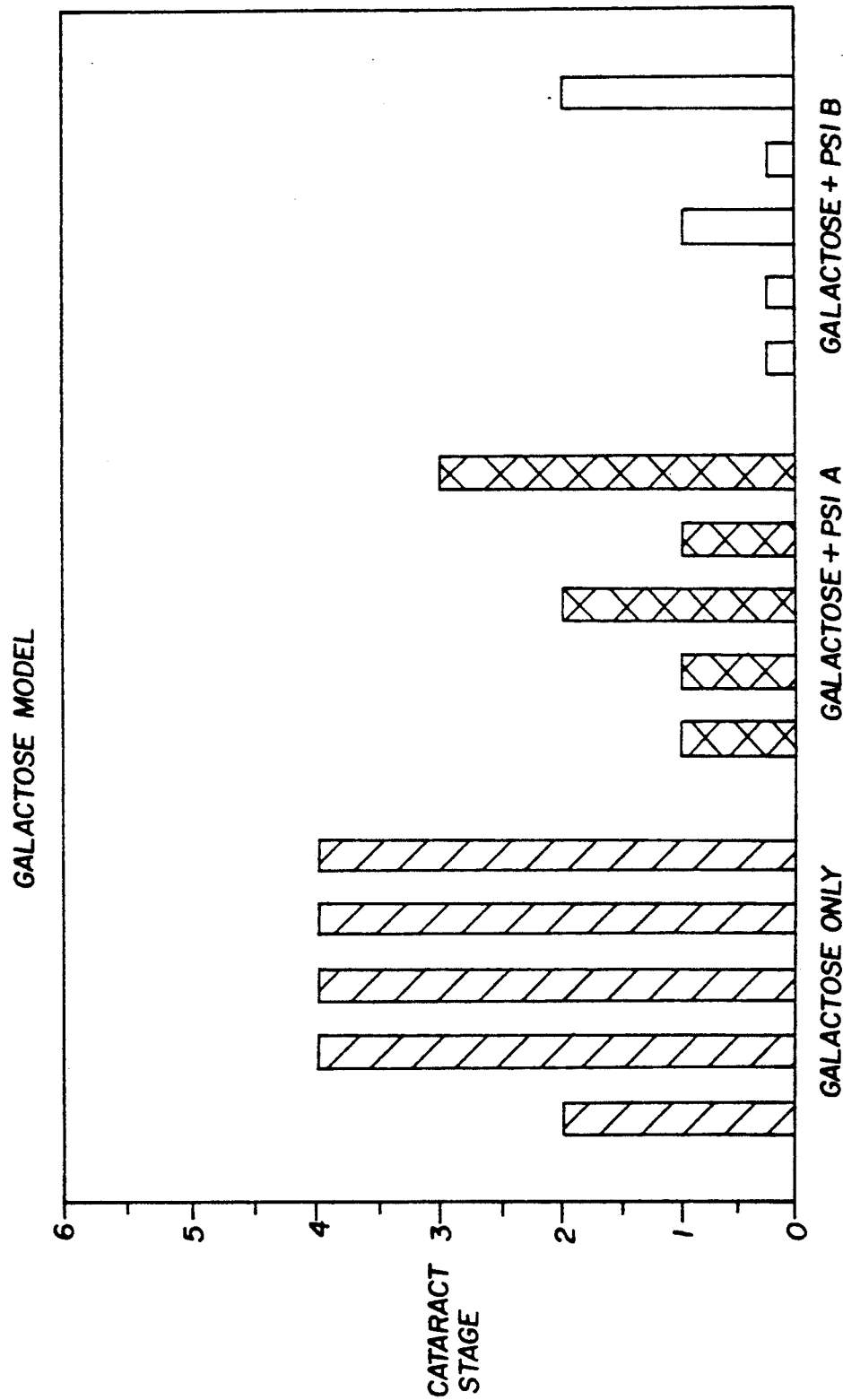
FIG. 20 is a graph of the effect of PSI A and B on galactose induced cataract.

FIG. 20 illustrates the effect of PSI A and B on galactose cataract 14 days after starting a galactose diet. PSI A had some inhibitory effect. PSI B was inhibitory in the galactose model. Observations were made approximately 14 days after start of the galactose diet.

Figure 21:
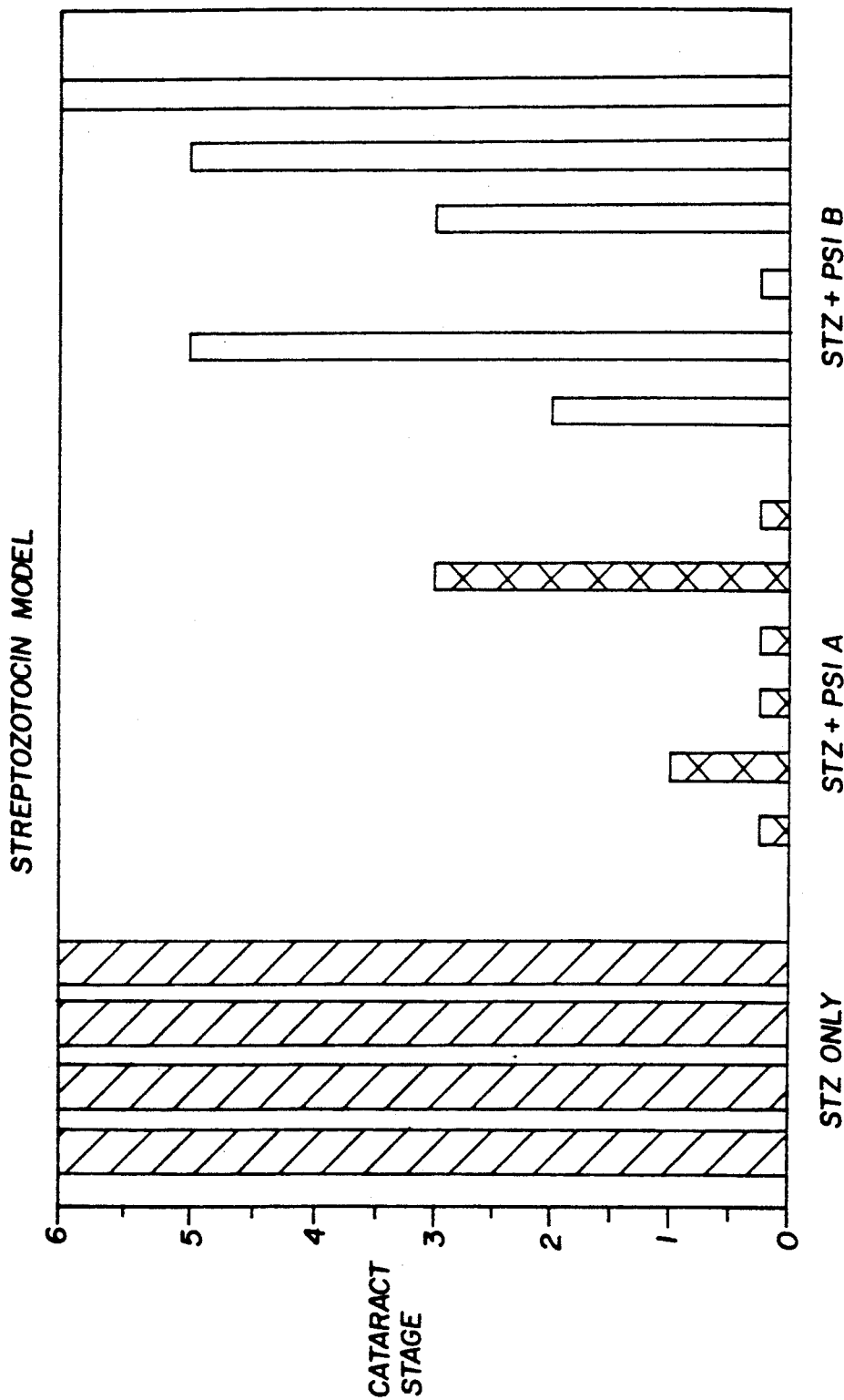
FIG. 21 is a graph of the effect of PSI A and B on streptozotocin induced cataract.

FIG. 21 depicts the effect of PSI A and B on streptozotocin cataract. PSI A inhibited cataract formation induced by streptozotocin. PSI B waS less effective in inhibited the streptozotocin cataract. Nearly 80% of the animals formed mature cataract 70 days after administration of streptozotocin in the absence of PSI.

Figure 22:
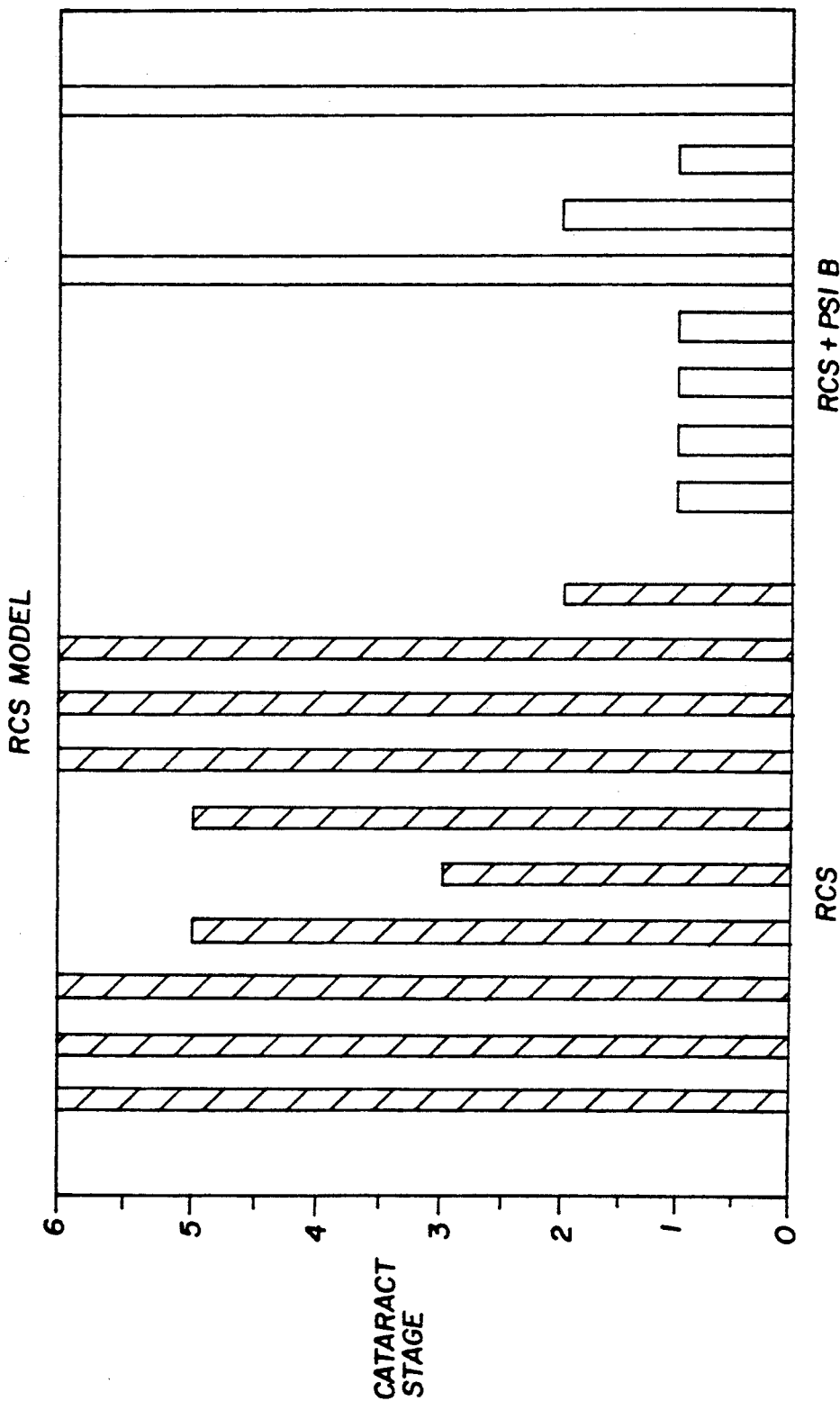
FIG. 22 is a graph of the effect of PSI A and B on RCS cataract.

FIG. 22 shows the effect of PSI B on RCS cataract. PSI B prevented cataract in approximately ⅔ of RCS animals 123 days after the animals were born.

EXAMPLE 24

Panthenol Inhibition of Selenium Cataract In Vivo

A single i.p. injection of 25 mg/kg of panthenol 15 minutes prior to selenite injection, as described in Example 7, prevented cataract formation in Sprague-Dawley rats. The eyes of the injected animals were examined daily using a slit-lamp biomicroscope for 7 days. Animals which received selenite only and no panthenol formed mature, stage 5 cataracts within 1 week of injection. Animals receiving the panthenol did not advance beyond stage 2.

EXAMPLE 25

Cysteamine Inhibition of Selenium Cataract In Vivo

A single i.p. injection of 58 mg/kg of cysteamine 15 minutes prior to selenite injection, as described in Example 7, prevented cataract formation in Sprague-Dawley rats. The eyes of the injected animals were examined daily using a slit-lamp biomicroscope for 7 days. Animals which received selenite only and no cysteamine formed mature, stage 5 cataracts within 1 week of injection. Animals receiving the cysteamine did not advance beyond stage 2.

EXAMPLE 26

A Natural Phase Separation Inhibitor for Prevention of Cataracts

Figure 23:
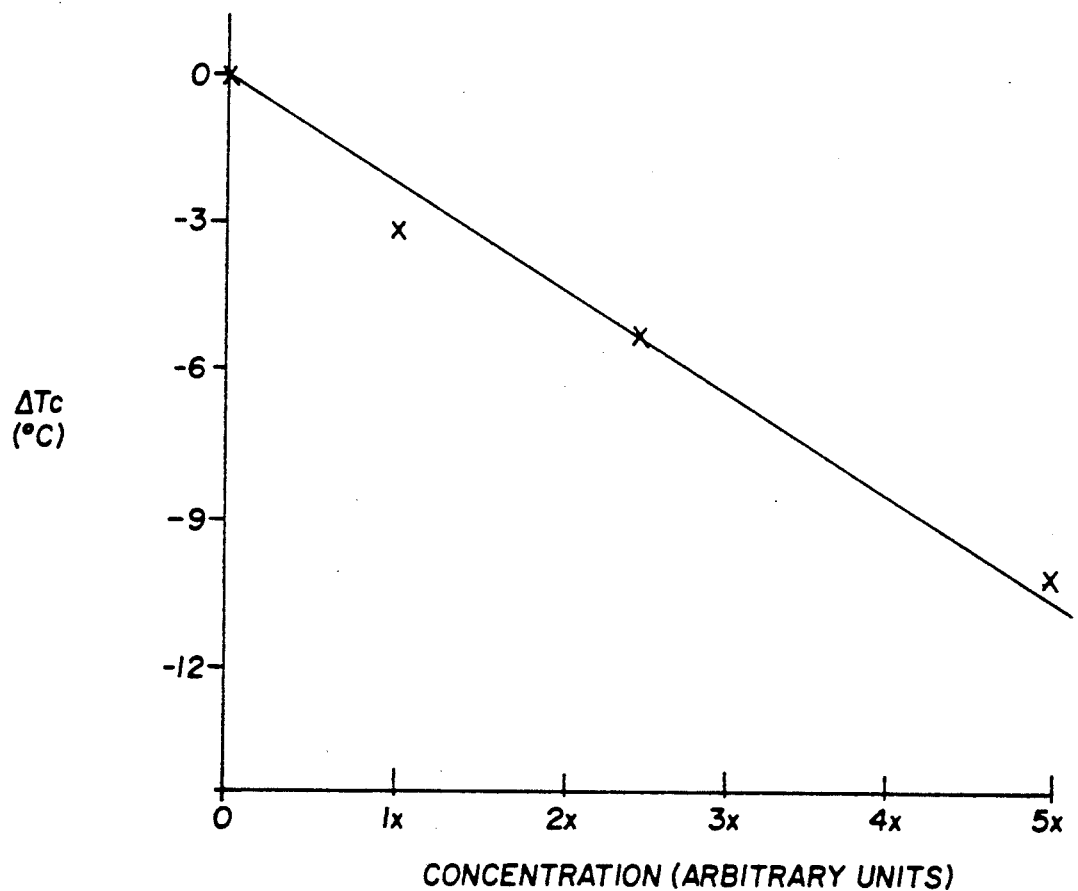
FIG. 23 is a graph of the change in phase separation temperature, Tc(°C.), versus concentration of naturally occurring phase separation inhibitor (arbitrary units and each data point representing the average of duplicative experiments).

A naturally occurring substance extracted from normal lens tissue having a molecular weight of less than 2000 Da has been used to decrease the phase separation temperature, Tc. FIG. 23 shows the strong inhibitory effect of the natural compound. The compound was added to lens homogenate as described in Example 2.

The substance was extracted from a lens homogenate which was centrifuged at approximately 250,000 g and the soluble supernatant filtered through a filter having a 2000 MW cutoff. It was important to prepare the homogenate without added buffer or salt, at physiological pH (7.0–7.2). The active compound is believed to be a metabolite in anaerobic glycolysis and is inactivated by a protease. On this basis, it is expected that the active compound may also be present in other natural sources including yeast and bacteria.

A natural reagent may have a variety of advantages: toxicity is less of a problem with a synthetic phase separation inhibitor; natural reagents may provide additional insight into the action of the phase inhibitors, in vivo; and natural reagents provide simple model compounds that can be modified to increase anti-cataract activity. The results illustrated in the above examples indicate that natural and physiologically compatible reagents have the potential to protect against and reverse cataract formation by acting as phase separation inhibitors.

Although the reagents of the present invention have been described with reference to traditional methods of administration, such as drops into the eye, in tablet form or by injection, other means familiar to those skilled in the art of drug delivery could be utilized. For example, drug encapsulated in polymer matrices could be implanted into or adjacent the eye for sustained linear release over time. Either degradable (for example, polyanhydrides, polyorthoesters, and polylactic acids) or nondegradable (for example, ethylene vinyl acetate and polystyrene) polymers could be used. Drug could also be injected directly into the aqueous humor, such as by microinjection.

Modifications and variations of the present invention, including methods and reagents for the prevention or reversal of cataract formation, will be obvious to those skilled in the art from the foregoing detailed description. Such modifications and variations are intended to come within the scope of the appended claims.

We claim:

1. A method for inhibiting cataractogenesis in an animal in need thereof, comprising administering to the animal a therapeutically or prophylactically effective amount of pantetheine.

* * * * *